(12) United States Patent
Tahara

(10) Patent No.: US 9,222,089 B2
(45) Date of Patent: Dec. 29, 2015

(54) AGING MARKER, METHOD FOR EVALUATING AGING INHIBITOR, AND CANCER INHIBITOR

(71) Applicant: Hiroshima University, Hiroshima (JP)

(72) Inventor: Hidetoshi Tahara, Hiroshima (JP)

(73) Assignee: HIROSHIMA UNIVERSITY, Hiroshima (JP)

( * ) Notice: Subject to any disclaimer, the term of this patent is extended or adjusted under 35 U.S.C. 154(b) by 0 days.

(21) Appl. No.: 14/091,268

(22) Filed: Nov. 26, 2013

(65) Prior Publication Data

US 2014/0088173 A1    Mar. 27, 2014

Related U.S. Application Data

(63) Continuation of application No. 13/518,378, filed as application No. PCT/JP2010/072592 on Dec. 15, 2010, now abandoned.

(30) Foreign Application Priority Data

Dec. 21, 2009 (JP) ................. 2009-288707

(51) Int. Cl.
  C12N 15/11 (2006.01)
  C12N 15/113 (2010.01)
  C12Q 1/68 (2006.01)

(52) U.S. Cl.
  CPC ............ C12N 15/113 (2013.01); C12Q 1/6876 (2013.01); C12Q 1/6886 (2013.01); *C12N 2310/141* (2013.01); *C12Q 2600/136* (2013.01); *C12Q 2600/158* (2013.01)

(58) Field of Classification Search
  CPC ................. C12N 15/113; C12N 2310/141
  See application file for complete search history.

(56) References Cited

U.S. PATENT DOCUMENTS

| 7,232,806 B2 | 6/2007 | Tuschl et al. | |
| 2009/0220969 A1 | 9/2009 | Chiang et al. | |
| 2010/0298407 A1* | 11/2010 | Mendell et al. | 514/44 A |
| 2012/0059043 A1* | 3/2012 | Lieberman et al. | 514/44 A |

FOREIGN PATENT DOCUMENTS

| JP | 2006-519008 | 8/2006 |
| JP | 2008-500837 | 1/2008 |
| JP | 2008-519606 | 6/2008 |
| WO | WO 2006/137941 | 12/2006 |
| WO | WO 2008/061537 | 5/2008 |

OTHER PUBLICATIONS

Pandey et al. Molecular and Cellular Biology Jul. 2009, 3783-3790.*
Alberts, et al.; "Molecular Biology of the Cell"; Fourth Edition, Newton Press, Inc.; pp. 1017-1018 (Dec. 20, 2004).
Boehm, et al; "A Developmental Timing MicroRNA and its Target Regulate Life Span in C. elegans"; Science; vol. 310, pp. 1954-1957 (Dec. 2005).
He, et al.; "Functional elucidation of MiR-34 in osteosarcoma cells and primary tumor samples"; Biochemical and Biophysical Research Communications; vol. 388, pp. 35-40 (Jul. 2009).
Lafferty-Whyte, et al.; "Pathway analysis of senescence-associated miRNA targets reveals common processes to different senescence induction mechanisms"; Biochimica et Biophysica Acta; pp. 341-352 (Feb. 2009).

* cited by examiner

*Primary Examiner* — Brian Whiteman
(74) *Attorney, Agent, or Firm* — Perkins Coie LLP; Viola T. Kung

(57) ABSTRACT

The present invention aims to elucidate a miRNA involved in cellular senescence and to provide a method of use thereof. The senescence marker of the present invention comprises a gene transcript of miR-22. Further, the method for evaluating a senescence inhibitor of the present invention comprises the step of measuring the expression level of a gene transcript of miR-22 in a sample in the presence of a test compound and in the absence of the test compound; and the step of comparing the expression level of the gene transcript of miR-22 in the sample in the presence of the test compound with the expression level of the gene transcript of miR-22 in the sample in the absence of the test compound. Further, the cancer inhibitor of the present invention comprises as an effective component a gene transcript of miR-22, which cancer inhibitor promotes cellular senescence and inhibits invasion and/or metastasis of cancer.

5 Claims, 16 Drawing Sheets

Sense:     aguucuucag-uggcaagcuuua
           ||||||||| ||||| ||||
Antisense: ugucaagaaguugaccgu-cgaa MCF-7 cell

AGING MARKER, METHOD FOR EVALUATING AGING INHIBITOR, AND CANCER INHIBITOR

CROSS REFERENCES TO RELATED APPLICATIONS

This is a continuation of U.S. application Ser. No. 13/518,378 filed Aug. 24, 2012, abandoned; which is a U.S. National Phase application of International Patent Application No. PCT/JP2010/072592, filed Dec. 15, 2010, and claims priority to Japanese Patent Application No. 2009-288707, filed Dec. 21, 2009, and Japanese Patent Application No. 2010-049928, filed Mar. 5, 2010, each of which is incorporated herein by reference in its entirety.

REFERENCE TO SEQUENCE LISTING, TABLE OR COMPUTER PROGRAM

The Sequence Listing is concurrently submitted herewith with the specification as an ASCII formatted text file via EFS-Web with a file name of Sequence Listing.txt with a creation date of Nov. 21, 2013, and a size of 768 bytes. The Sequence Listing filed via EFS-Web is part of the specification and is hereby incorporated in its entirety by reference herein.

TECHNICAL FIELD

The present invention relates to a senescence marker and a method for evaluating a senescence inhibitor using as an index the expression level of hsa-miR-22, and a cancer inhibitor using a cellular senescence promoting action of hsa-miR-22.

BACKGROUND ART

MicroRNAs (hereinafter referred to as miRNAs) are short non-coding RNAs identified in the genomes of a wide variety of species. miRNAs were first discovered in 1993 in *Caenorhabditis elegans*, and this was followed by discovery of miRNAs in many other multicellular organisms. A miRNA is a negative regulator of gene expression, and considered to function mainly by incomplete interaction of base pairs with a sequence in the 3'-untranslated region of a protein-encoding mRNA. Various miRNAs so far known, including those of humans, are registered in miRBase (see http://www.mirbase.org/). The roles of some of these miRNAs are not known. However, it has been revealed that certain miRNAs are involved in regulation of various cellular processes, such as differentiation of adipocytes, maturation of oocytes, maintenance of the pluripotent cellular state and regulation of insulin secretion.

For example, Patent Literature 1 describes a method for regulating expression of a target gene in cells, which method comprises the step of introducing a polynucleotide that forms a double strand with mRNA transcribed from the target gene into the cells. In this method, the region where the double strand is formed comprises a mammalian miRNA target region. It is described that examples of the polynucleotide used in this method include various miRNAs and precursors thereof (pre-miRNAs).

Further, Patent Literature 2 describes various methods and compositions in which miRNAs are involved. More particularly, for example, a method wherein expression analysis of miRNAs is carried out to produce a miRNA profile, and the produced miRNA profile is then used as described. In this method, many miRNAs which may be used to produce usable profiles are described. For example, among these many miRNAs, (hsa-)miR-22 is included. (hsa-)miR-22 is a known miRNA also registered in the above-mentioned miRBase. Patent Literature 2 also describes that these many miRNA profiles can be used for diagnosis of specific diseases, diseased states and disorders. Examples of the specific diseases include cancer.

Further, Patent Literature 3 describes a method and a composition based on a more detailed mechanism, wherein a miRNA or a miRNA inhibitor molecule is involved. More particularly, the literature describes a method for reducing or inhibiting the cell growth, a method for inducing or increasing the cell growth, a method for decreasing the cell survival rate, a method for increasing the cell survival rate, a method for increasing apoptosis of cells, and a method for inhibiting apoptosis of cells, which methods comprise the step of introducing an effective amount of a specific synthetic miRNA molecule to cells.

Patent Literature 3 also partially describes functions of the above-mentioned (hsa-)miR-22 among such miRNAs. More particularly, it is described that (hsa-)miR-22 is a miRNA which significantly decreases the number of living A549 cells (human lung cancer cells) and significantly increases the percentage of apoptotic cells. Further, a method for treating cancer in a subject, which method uses such a function and comprises the step of administration of an effective amount of a synthetic miRNA molecule corresponding to (hsa-)miR-22 to the subject, is also described.

On the other hand, precursor cells of most animal cells stop their growth after specific numbers of times of division, and remain in the terminally-differentiated state. The mechanism to stop the division has not been completely elucidated. However, such a cell growth inhibition mechanism in the cell has been elucidated to some extent for human fibroblasts. More particularly, it has been revealed that the growth rate decreases in the late mitotic period, and the cells then stop dividing and enter a non-dividing state, in which the cells never grow again. This phenomenon is called cellular senescence due to replication (see Non-patent Literature 1).

PRIOR ART DOCUMENTS

Patent Literatures

[Patent Literature 1] National Publication No. 2006-519008
[Patent Literature 2] National Publication No. 2008-500837
[Patent Literature 3] National Publication No. 2008-519606

Non-Patent Literature

[Non-Patent Literature 1] Bruce Alberts, Alexander Johnson, Julian Lewis, Martin Raff, Keith Roberts, and Peter Walter (translation supervisors: Keiko Nakamura and Kenichi Matsubara), MOLECULAR BIOLOGY OF THE CELL FORTH EDITION, Newton Press, Inc., Dec. 20, 2004, pp. 1017-1018.

DISCLOSURE OF INVENTION

Problems to be Resolved by the Invention

The mechanism and meaning of the above-mentioned induction of cellular senescence due to replication, including the relationship with aging of individuals, have been controversial for a long time. This is because cellular senescence is considered to be an important biological defense mechanism along with apoptosis, and a new application of cellular senescence to cancer therapy is therefore expected. That is, this is because, similarly to apoptosis, cellular senescence is involved in the cell growth and a protection mechanism against abnormal cells. Thus, elucidation of genes involved in cellular senescence has been demanded. It is expected that elucidation of a gene involved in cellular senescence will enable not only an application of cellular senescence to a new cancer therapy but also development of a senescence marker or senescence inhibitor using the gene.

On the other hand, as described above, Patent Literature 2 suggests the possibility of a use of a profile of (hsa-)miR-22, as one of the profiles of many miRNAs, in diseases such as cancer. However, whether (hsa-)miR-22 can be used for diseases such as cancer has not been elucidated in detail based on Examples or in view of the mechanism.

In Patent Literature 3, a method for treating cancer using (hsa-)miR-22 is described based on a concrete mechanism. More particularly, as mentioned above, it is described that the method for treating cancer is carried out by increasing apoptotic cells to decrease the number of living cancer cells (A549 cells; human lung cancer cells). However, according to an intensive study by the present inventors, introduction of hsa-miR-22 to cancer cells other than A549 cells (SiHa cells and MCF-7 cells) did not cause remarkable increase in apoptotic cells.

The present invention was made under the above-described circumstances, and aims to elucidate a miRNA involved in cellular senescence and to provide a method for using the miRNA. More particularly, the present invention aims to provide a senescence marker with which the degree of senescence of a sample can be judged, a method for evaluating a senescence inhibitor with which a substance that can inhibit senescence can be easily evaluated, and a cancer inhibitor that causes senescence of cells to inhibit growth, invasion and/or metastasis of cancer.

Means for Solving the Problems

The senescence marker of the first embodiment of the present invention comprises a gene transcript of miR-22.

The gene transcript of miR-22 preferably comprises RNA with the base sequence shown in SEQ ID NO:1, RNA with the base sequence shown in SEQ ID NO:2, and/or RNA with the base sequence shown in SEQ ID NO:3.

Further, the gene transcript of miR-22 comprises Pre-hsa-miR-22 and/or double-stranded hsa-miR-22.

The method of the second embodiment of the present invention for evaluating a senescence inhibitor comprises:

the step of measuring the expression level of a gene transcript of miR-22 in a sample in the presence of a test compound and in the absence of the test compound; and the step of comparing the expression level of the gene transcript of miR-22 in the sample in the presence of the test compound with the expression level of the gene transcript of miR-22 in the sample in the absence of the test compound.

The gene transcript of miR-22 preferably comprises RNA with the base sequence shown in SEQ ID NO:1, RNA with the base sequence shown in SEQ ID NO:2, and/or RNA with the base sequence shown in SEQ ID NO:3.

More preferably, the sample is derived from a mammalian subject.

Still more preferably, the sample is a human fibroblast(s).

The cancer inhibitor of the third embodiment of the present invention comprises as an effective component a gene transcript of miR-22, which cancer inhibitor promotes cellular senescence and inhibits invasion and/or metastasis of cancer.

Preferably, the gene transcript of miR-22 comprises RNA with the base sequence shown in SEQ ID NO:1, RNA with the base sequence shown in SEQ ID NO:2, and/or RNA with the base sequence shown in SEQ ID NO:3.

Further, preferably, the gene transcript of miR-22 comprises Pre-hsa-miR-22 and/or double-stranded hsa-miR-22.

More preferably, the cancer inhibitor is a gastric cancer inhibitor, uterine cancer inhibitor, pharyngeal cancer inhibitor, breast cancer inhibitor, cervical cancer inhibitor and/or colon cancer inhibitor.

Still more preferably, the cancer inhibitor is a cervical cancer inhibitor and/or breast cancer inhibitor.

Effect of the Invention

With the senescence marker of the first embodiment of the present invention, the degree of senescence of a sample can be judged. By the method of the second embodiment of the present invention for evaluating a senescence inhibitor, a substance that inhibits senescence can be easily evaluated. With the cancer inhibitor of the third embodiment of the present invention, cellular senescence can be promoted to inhibit the growth, invasion and/or metastasis of cancer.

MODE FOR CARRYING OUT THE INVENTION

As a result of intensive study by the present inventors, it was elucidated that (hsa-)miR-22 is a miRNA involved in cellular senescence and can be utilized, taking advantage of the cellular senescence, for inhibition of the growth, invasion and metastasis of cancer cells (see Examples described below). (hsa-)miR-22 is a known miRNA as described above, and, for details of (hsa-)miR-22, one may refer to miRBase (http://www.mirbase.org/). For example, in terms of hsa-miR-22, which is miR-22 in humans, its stem-loop sequence is registered under the accession number MI0000078; its mature sequence is registered under the accession number MIMAT0000077; and its Minor miR* sequence is registered under the accession number MIMAT0004495; in miRBase. The stem-loop sequence of hsa-miR-22 is shown in SEQ ID NO:1; the mature sequence is shown in SEQ ID NO:2; and the Minor miR* sequence is shown in SEQ ID NO:3.

Figures 1, 2:
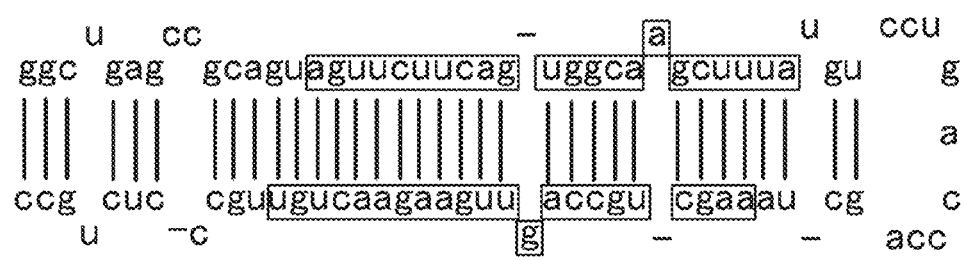
FIG. 1 is a schematic diagram showing the stem-loop structure of hsa-miR-22 (SEQ ID NO: 1) of the present invention.
FIG. 2 is a schematic diagram showing the structure of double-stranded hsa-miR-22 (Sense: SEQ ID NO: 3, Antisense: SEQ ID NO: 2)

FIG. 1 is a schematic diagram showing the stem-loop structure of hsa-miR-22 of the present invention. That is, FIG. 1 shows an hsa-miR-22 precursor (Pre-hsa-miR-22), which is an unprocessed gene transcript of hsa-miR-22. In the present description, "hsa-miR-22 precursor" and "Pre-hsa-miR-22" mean a miRNA having the stem-loop structure shown in FIG. 1 or miRNA shown in SEQ ID NO:1.

FIG. 2 is a schematic diagram showing the structure of double-stranded hsa-miR-22. In the present description, "double-stranded hsa-miR-22" means a double-stranded miRNA having the structure shown in FIG. 2. Further, in the present description, "mature hsa-miR-22" means the mature miRNA shown in SEQ ID NO:2 or SEQ ID NO:3. The "mature hsa-miR-22" shown in SEQ ID NO:2 may also be simply referred to as "hsa-miR-22". The "mature hsa-miR-22", with the sequence shown in SEQ ID NO:3, may be used in the same manner as the term "hsa-miR-22*". By formation of a double strand by hsa-miR-22 and hsa-miR-22*, double-stranded hsa-miR-22 is constituted.

The meaning of the term "gene transcript of hsa-miR-22" includes "Pre-hsa-miR-22", "double-stranded hsa-miR-22", "hsa-miR-22" and "hsa-miR-22*" as shown in the above-mentioned FIG. 1, FIG. 2, SEQ ID NO:1, SEQ ID NO:2 and SEQ ID NO:3. When a gene transcript is simply referred to as "gene transcript of miR-22", the meaning of the term includes not only "gene transcript of hsa-miR-22", but also "gene transcript of miR-22" in a non-human organism.

Embodiments of the present invention will now be described in detail. The present invention is not restricted to the embodiments, and various embodiments are possible within the scope of the present invention. In the present description, the meaning of the expressions "comprise" and "contain" also includes "composed of" and "constituted by".

(Senescence Marker)

The embodiment 1 of the present invention relates to a senescence marker. As described in detail in Examples, as a result of intensive study by the present inventors, it was confirmed that a gene transcript of (hsa-)miR-22 is highly expressed in senescent human fibroblasts. It was further revealed that the expression level of the gene transcript of (hsa-)miR-22 increases as senescence proceeds. Thus, the senescence marker of the embodiment 1 comprises the gene transcript of miR-22. More particularly, the gene transcript of miR-22 comprises RNA with the base sequence shown in SEQ ID NO:1, RNA with the base sequence shown in SEQ ID NO:2, and/or RNA with the base sequence shown in SEQ ID NO:3. Examples of the senescence marker of the embodiment 1 comprising RNA with the base sequence shown in SEQ ID NO:1, RNA with the base sequence shown in SEQ ID NO:2, and/or RNA with the base sequence shown in SEQ ID NO:3 include Pre-hsa-miR-22 and double-stranded hsa-miR-22.

Examples of uses of the senescence marker of the embodiment 1 include a method for judging the degree of senescence, which method comprises the step of comparing the expression level of a gene transcript of miR-22 with a standard value of the expression level of the gene transcript of miR-22 corresponding to the sample.

In the present description, the term "sample" means an arbitrary sample to be used as a biological subject for which the expression level of a gene transcript of miR-22 can be measured to judge the degree of senescence. The sample is preferably derived from a mammalian subject. The sample is most preferably human (*Homo sapiens*) fibroblasts. The "standard value of the expression level of the gene transcript of miR-22 corresponding to the sample" means a value to be used as a standard with which the value of the expression level of the gene transcript of miR-22 measured for the sample can be compared. For example, the standard value is a mean value of the gene transcript of miR-22, which was preliminarily measured for samples in each age group (including the age group of cells). The expression level of the gene transcript of miR-22 in the samples in each age group may be measured at intervals of an arbitrary number of hours, days or years. The mean value may be calculated by any calculation method, and examples of the mean value include the arithmetic mean, geometric mean, and harmonic mean. Calculation of such a standard value, or a mean value in each age group in advance can be easily carried out by using a method known to those in the art for measuring the expression level of miRNA, such as the method described later.

For example, in cases where the sample is from a human subject or human-derived cells, the expression level of a gene transcript of hsa-miR-22 is measured in advance for a plurality of human subjects in the same age group, or for cells in the same age group. After calculating such a mean value, the calculated mean value is used as the standard value. As mentioned above, the expression level of the gene transcript of (hsa-)miR-22 increases as senescence proceeds. Therefore, when the expression level in a sample is compared with the standard value, in cases where the expression level in the sample is larger than the standard value, the sample can be said to be senescent. Further, it can be said that the larger the difference between the expression level in the sample and the standard value, the more senescent the sample.

For more accurate judgment of senescence, in cases where the degree of senescence of human fibroblasts is to be judged, the expression level of the gene transcript of hsa-miR-22 in each of age groups (at intervals of 5 years, for example) is preliminarily measured to calculate the mean value. Thereafter, the expression level of the gene transcript of hsa-miR-22 in human fibroblasts which is to be used as the sample is measured. By comparing the expression level measured for the sample with the above-described mean value of the expression level measured in each age group, the age group in which the mean value of the expression level is closest to the expression level measured for the sample is determined. Based on comparison between the determined age group and the age group from which the sample came, the degree of senescence of the sample human fibroblasts can be judged. That is, it can be said that the older the determined age group relative to the actual age group, the more senescent the sample human fibroblasts (cellular senescence).

Such a method for judging senescence comprises the step of measuring the expression level of the gene transcript of miR-22 in a sample. The method for measuring the expression level of the gene transcript of miR-22 may be any method as long as it is a method known to those in the art for measuring the expression level of miRNA. The measurement is preferably carried out by any method selected from Northern blotting, RT-PCR (Reverse Transcription Polymerase Chain Reaction), real-time RT-PCR, RT-LAMP (Reverse Transcription Loop-Mediated Isothermal Amplification), microarray analysis and in situ hybridization. The measurement is most preferably carried out using real-time RT-PCR.

Thus, with the senescence marker of the embodiment 1, the degree of cellular senescence can be judged by measuring the expression level of the gene transcript of miR-22 in a sample (biological subject sample) and comparing the measured value with a standard value of the expression level of the gene transcript of miR-22 corresponding to the sample. Further, by preliminarily measuring the expression level of the gene transcript of miR-22 in each age group to calculate the mean value, more accurate diagnosis of senescence is possible. Still further, the fact that the degree of cellular senescence can be judged may lead to development of novel pharmaceutical compositions, and to more accurate diagnosis of the degree of progress of a disease condition and the like.

The cells to which the senescence marker of the embodiment 1 is to be applied are not restricted to human fibroblasts. The gene transcript of miR-22 is considered to be highly expressed in various senescent cells. For example, the gene transcript is considered to be highly expressed also in senescent stem cells. Since senescent cells also affect immunity and the like, it is suggested that, with the senescence marker of the embodiment 1, for example, by using the above method for judging senescence, the immunity, cell renewal capacity, prognosis after living donor liver transplantation, and the like of a sample can be judged. The "standard value of the expression level of the gene transcript of miR-22 corresponding to the sample" is preferably preliminarily determined in consideration of the type of the cells for which the expression level was measured and the type of judgment.

Further, the senescence marker of the embodiment 1 may be used for a kit for judging senescence (cellular senescence). The kit for judging senescence may comprise at least one of primers and probes which can specifically hybridize with the gene transcript of miR-22. Those skilled in the art can appropriately design such primers and probes based on the base sequence of the gene transcript of miR-22 by reference to information in the above-described database or the like.

Preferably, the number of bases in the base sequence of each primer or probe is appropriately determined such that specific binging with a template is possible. For example, the primer or probe has several ten bp, more particularly, about 15 to 30 bp. Further, it is also important to design the base sequence such that no hairpin structure is formed in the primer and annealing between the sense strand and the antisense strand does not occur. For example, commercially available software for designing primers, such as Oligo™ (manufactured by National Bioscience Inc.) may be used.

Such a kit for judging senescence (cellular senescence) may comprise equipment for measuring the expression level of the gene transcript of miR-22. The "equipment" means a factor, component and/or the like known to those skilled in the art, which is necessary for measuring the expression level of miRNA. The type of the equipment varies depending on the principle of the measurement of the expression level of the gene transcript of miR-22, and examples of the equipment include various reagents, enzymes, buffers and reaction plates (containers).

Examples of the principle of the measurement of the expression level of the gene transcript of miR-22 include, similarly to the above judging method, Northern blotting, RT-PCR, real-time RT-PCR, RT-LAMP, microarray analysis and in situ hybridization. The principle is most preferably real-time RT-PCR.

The kit for judging senescence (cellular senescence) may further comprise manufacturer's instructions and/or the like that describe a standard value (for example, the mean value of the expression level of the gene transcript of miR-22 in samples from each age group) as mentioned above with which the expression level of the gene transcript of miR-22 in a sample can be compared.

In such a case, based on comparison the expression level of the gene transcript of miR-22 in a sample (cells or the like) measured using the above-described equipment or the like with the standard value, senescence (cellular senescence) can be judged by one time of measurement of the expression level. Thus, with the kit for judging senescence (cellular senescence) using the senescence marker of the embodiment 1, the degree of senescence of a sample can be easily judged.

(Method for Evaluating Senescence Inhibitor)

The embodiment 2 of the present invention relates to a method for evaluating a senescence inhibitor. More particularly, the embodiment 2 relates to a method for evaluating a senescence inhibitor, which method comprises the step of measuring the expression level of a gene transcript of miR-22 in a sample in the presence of a test compound and in the absence of the test compound; and the step of comparing the expression level of the gene transcript of miR-22 in the sample in the presence of the test compound with the expression level of the gene transcript of miR-22 in the sample in the absence of the test compound.

As described in embodiment 1, the gene transcript of miR-22 comprises RNA with the base sequence shown in SEQ ID NO:1, RNA with the base sequence shown in SEQ ID NO:2, and/or RNA with the base sequence shown in SEQ ID NO:3. The gene transcript of miR-22 may further comprise Pre-hsa-miR-22 and/or double-stranded hsa-miR-22. The "sample" is preferably a sample derived from a mammalian subject, more preferably human fibroblasts. In the present description, meanings of the terms such as "evaluation method" "evaluate" and "evaluation" also include screening.

As described above, as senescence proceeds, the expression level of the gene transcript of miR-22 increases. Therefore, by measuring the expression level of the gene transcript of miR-22 in the presence and in the absence of a test compound and comparing the measured values, whether or not the test compound is a senescence inhibitor can be evaluated and screened.

More particularly, in cases where the expression level of the gene transcript of miR-22 in the presence of a test compound (which was mixed with or added to the sample) is smaller than the expression level of the gene transcript of miR-22 in the absence of the test compound, the test compound can be evaluated as a senescence inhibitor. Further, as in the above-described embodiment 1, it can be said that the larger or smaller the difference between the expression levels observed in the presence of the test compound and in the absence of the test compound, the larger or smaller the senescence inhibition action of the test compound. Further, the judgment does not need to be carried out based on the difference between those expression levels, and may be carried out by calculating the age groups based on the expression levels observed in the presence of the test compound and in the absence of the test compound and comparing the calculated age groups.

The method for measuring the expression level of the gene transcript of miR-22 in a sample is not restricted as long as the method is one which is known to those in the art for measuring the expression level of miRNA. Similarly to embodiment 1, the measurement is preferably carried out by using any method selected from Northern blotting, RT-PCR, real-time RT-PCR, RT-LAMP, microarray analysis and in situ hybridization. The measurement is most preferably carried out by real-time RT-PCR.

Thus, by the method for evaluating a senescence inhibitor of the embodiment 2, substances that can inhibit senescence can be easily evaluated and selected. The selected senescence inhibitors may be used as components for cosmetics, nutritional supplements and the like, as well as for various purposes. Further, in cases where a substance was not judged to be a senescence inhibitor but was judged instead to be a senescence promoter in the embodiment 2, addition of the substance as a component for cosmetics, nutritional supplements or the like can be avoided.

(Cancer Inhibitor)

The embodiment 3 of the present invention relates to a cancer inhibitor comprising as an effective component a gene transcript of miR-22. More particularly, the gene transcript of miR-22 comprises RNA with the base sequence shown in SEQ ID NO:1, RNA with the base sequence shown in SEQ ID NO:2, and/or RNA with the base sequence shown in SEQ ID NO:3; promotes cellular senescence; and inhibits invasion and/or metastasis of cancer. As described in embodiment 1 and embodiment 2, the gene transcript of miR-22; or RNA with the base sequence shown in SEQ ID NO:1, RNA with the base sequence shown in SEQ ID NO:2, and/or RNA with the base sequence shown in SEQ ID NO:3; include(s) Pre-hsa-miR-22 and double-stranded hsa-miR-22.

In the present description, "cancer inhibitor" means a composition which promotes senescence (cellular senescence) of cancer cells and, as a result, inhibits the growth, invasion and/or metastasis of cancer. The cancer inhibitor of the embodiment 3 of the present invention is not restricted, and preferably a gastric cancer inhibitor, uterine cancer inhibitor, pharyngeal cancer inhibitor, breast cancer inhibitor, cervical cancer inhibitor and/or colon cancer inhibitor. Among these, the cancer inhibitor is most preferably a cervical cancer inhibitor and/or breast cancer inhibitor.

The gene transcript of miR-22 as described above may be any of an artificially chemically synthesized transcript, a biochemically synthesized transcript, and a transcript synthesized in vivo.

The cancer inhibitor of the embodiment 3 can be produced by blending a gene transcript of miR-22 as an effective component into a base which is normally used for agents for gene therapy. In cases where the gene transcript of miR-22 is incorporated in a virus vector, the cancer inhibitor can be produced by preparing virus particles containing the recombinant vector and blending the virus particles into a base which is normally used for agents for gene therapy.

As the base into which the gene transcript of miR-22 as an effective component is blended, a base normally used for injection solutions may be used. Examples of the base include distilled water; salt solutions of sodium chloride and mixtures of sodium chloride and an inorganic salt; solutions of mannitol, lactose, dextran, glucose and/or the like; solutions of amino acids such as glycine and/or arginine; organic acid solutions; and mixed solutions of a salt solution and a glucose solution. Alternatively, according to a conventional method known to those skilled in the art, an injection solution may be prepared as a solution, suspension or dispersion using an auxiliary agent(s) such as an osmotic pressure regulator, pH adjuster, vegetable oil and/or surfactant. Such an injection solution may be prepared, by an operation such as pulverization or freeze-drying, as a formulation to be dissolved upon use.

The dosage form of the cancer inhibitor of the embodiment 3 may be either systemic administration such as intravenous or intra-arterial injection, or local administration such as local injection or oral administration. Further, the dosage form may be a combination with the catheter technique, transgenic technology or surgery. That is, examples of the administration method of the cancer inhibitor of the embodiment 3 include oral administration, parenteral administration (e.g., intravenous administration, intramuscular administration, subcutaneous administration, intradermal administration, mucosal administration, rectal administration, vaginal administration, local administration to the affected area and transdermal administration) and direct administration to the affected area.

In cases where the cancer inhibitor of the embodiment 3 is used as a pharmaceutical composition, the cancer inhibitor may be blended as required with a pharmaceutically acceptable additive(s). Examples of the pharmaceutically acceptable additive(s) include, but are not limited to, antioxidants, preservatives, coloring agents, flavoring agents, diluents, emulsifiers, suspending agents, solvents, fillers, bulking agents, buffers, delivery vehicles, diluents, carriers, vehicles and pharmaceutical adjuvants.

The formulation of the cancer inhibitor of the embodiment 3 is not restricted, and examples of the formulation include liquids, injection solutions and sustained preparations. The solvent to be used for preparing such a formulation may be either aqueous or nonaqueous.

The gene transcript of miR-22 as an effective component of the cancer inhibitor of the embodiment 3 may be introduced using, for example, a method for introduction of nucleic acid molecules using liposomes (e.g., the liposome method, HVJ-liposome method, cationic liposome method, lipofection method or lipofectamine method), microinjection, or a method for transferring nucleic acid molecules into cells together with carriers (metal particles) using a gene gun. A viral vector such as a recombinant adenovirus or retrovirus may also be used. More particularly, by incorporating the gene transcript of miR-22 into a detoxicated DNA virus or RNA virus such as a retrovirus, adenovirus, adeno-associated virus, herpes virus, vaccinia virus, pox virus, poliovirus, Sindbis virus, Sendai virus or SV40, and infecting cells or a tissue with the resulting recombinant virus, the gene can be introduced into the cells or tissue.

The dose of the cancer inhibitor of the embodiment 3 may be determined by those skilled in the art in consideration of the purpose of use; severity of the disease; age, body weight, sex and/or past history of the patient; and/or the like. Thus, by using a cancer inhibitor comprising as an effective component the gene transcript of miR-22 of the embodiment 3, senescence of cancer cells is promoted, and, as a result, growth of the cancer can be inhibited, and further, invasion and metastasis of the cancer can be inhibited. This means that, although the cancer inhibitor of the embodiment 3 causes senescence of normal cells, the cancer inhibitor hardly causes apoptosis of normal cells (see Examples). That is, it is suggested that miR-22 is more effective and practical as an effective component of a cancer inhibitor compared to many other miRNAs equivalently listed in Patent Literature 2 and Patent Literature 3. Thus, it is also suggested that side effects caused by administration of the cancer inhibitor of the embodiment 3 may be much less severe than those of conventional anti-cancer agents.

The present invention is described in more detail by way of Examples below, but the present invention is not limited by the Examples.

EXAMPLES

The present inventors studied miRNAs involved in cellular senescence, inhibition of cell growth and/or the like. As a result, it was discovered that the gene transcript of (hsa-)miR-22 (see miRBase, http://www.mirbase.org/) is involved in cellular senescence and inhibition of the cell growth, and that the inhibition of the cell growth can be used to inhibit the growth, invasion and metastasis of cancer. For details of miR-22, one may refer to the above-described accession number in miRBase.

Example 1

Example 1 describes an example in relation to the expression levels of hsa-miR-22* in young and senescent human fibroblasts. The present inventors investigated the expression levels of hsa-miR-22* in young human fibroblasts and senescent human fibroblasts (cells that experienced a larger number of times of division than young cells) by quantitative real-time RT-PCR. Details of the investigation are described below.

The expression level of hsa-miR-22* was investigated for human fibroblasts TIG-3 cells, TIG-1 cells, TIG-112 cells, TIG-114 cells and MRC-5 cells. The TIG-3 cells, TIG-1 cells, TIG-112 cells and TIG-114 cells were cultured using DMEM (Dulbecco's Modified Eagle's Medium) supplemented with 10% FBS (Fetal Bovine Serum) and an antibiotic. The MRC-5 cells were cultured in DMEM/F-12 medium (1:1, v/v) supplemented with SAP (0.2 mM serine, 0.1 mM aspartic acid, 1.0 mM pyruvate), 10% FBS and an antibiotic. All these cells were cultured using a humidified incubator at 37° C. under 5% $CO_2$.

Subsequently, RNA was recovered from these cultured cells and quantitative real-time RT-PCR was carried out. First, total RNA of the cultured cells was extracted according to the protocol for miRVana miRNA Isolation Kit (Ambion), and quantified with a Nanodrop spectrophotometer. cDNA was synthesized from 10 ng of the total RNA. The expression level of miRNA was quantified using Taqman microRNA assays (Applied Biosystem). The quantitative real-time RT-PCR was carried out using ABI Step One and Step One Plus real-time PCR system (Applied Biosystem) and LightCycle 480 (Roche). The expression level of miRNA was determined based on the threshold cycle and standardized using U6 small nuclear RNA, followed by calculating a relative expression level by the $2^{-\Delta\Delta Ct}$ method taking the value in the young cells as 1.

Figure 3:
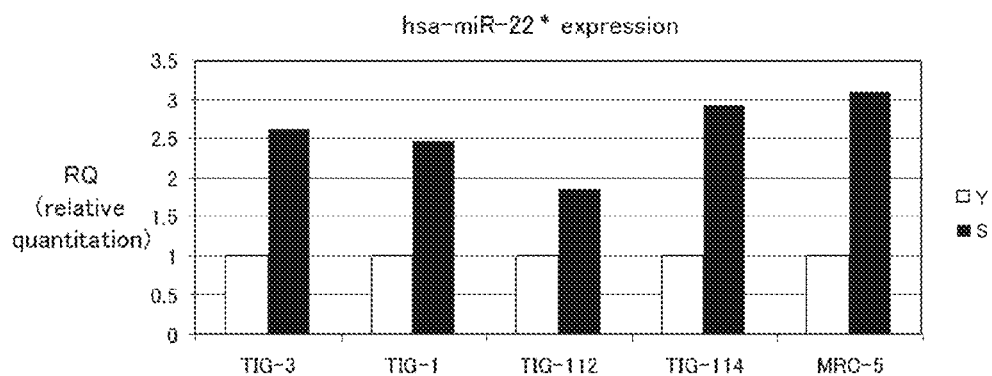
FIG. 3 is a diagram showing data on the expression level of hsa-miR-22* in human fibroblasts measured by qRT-PCR in Example 1.

FIG. 3 is a diagram showing data on the expression level of hsa-miR-22* in human fibroblasts measured by qRT-PCR in Example 1. For each strain of senescent cells (S), a relative value calculated taking the value in young cells (Y) as 1 (RQ (relative quantitation)) is shown. As shown in FIG. 3, in any of the human fibroblast strains, senescent cells (S) show a higher expression level of hsa-miR-22* compared to young cells (Y). This result suggests that, during the course of senescence of cells (by repeating division many times), as the degree of senescence increases, the expression level of hsa-miR-22*, that is, the gene transcript of miR-22, increases.

Example 2

The present Example 2 describes an example in relation to cases where double-stranded hsa-miR-22 was introduced into human fibroblasts. The present inventors investigated whether or not phenomena found in senescent cells are observed when double-stranded hsa-miR-22 was introduced into human fibroblasts (MRC-5 cells). Details of the investigation are described below.

First, the present inventors investigated whether or not formation of senescence-associated heterochromatic foci (hereinafter referred to as SAHF), which is a marker for senescent cells, is observed in cases where double-stranded hsa-miR-22 was introduced into human fibroblasts (MRC-5 cells). According to the protocol for Lipofectamine RNAi Max (Invitrogen), 10 nM double-stranded hsa-miR-22 (B-bridge, this also applies to later-mentioned Examples) or AllStars Negative Control siRNA (Qiagen) was introduced into MRC-5 cells. The introduction efficiency was assumed to be not less than 90% based on measurement using fluorescently-labeled double-stranded short interference RNA. The cells were plated in an 8-well culture chamber or 35-mm dish 48 hours after the introduction. Four days later, the cells were washed twice by addition of PBS (phosphate buffer saline), and PBS supplemented with 2% formaldehyde was then added to the cells. Thereafter, the cells were incubated for 5 days at room temperature for fixation.

Figure 4:
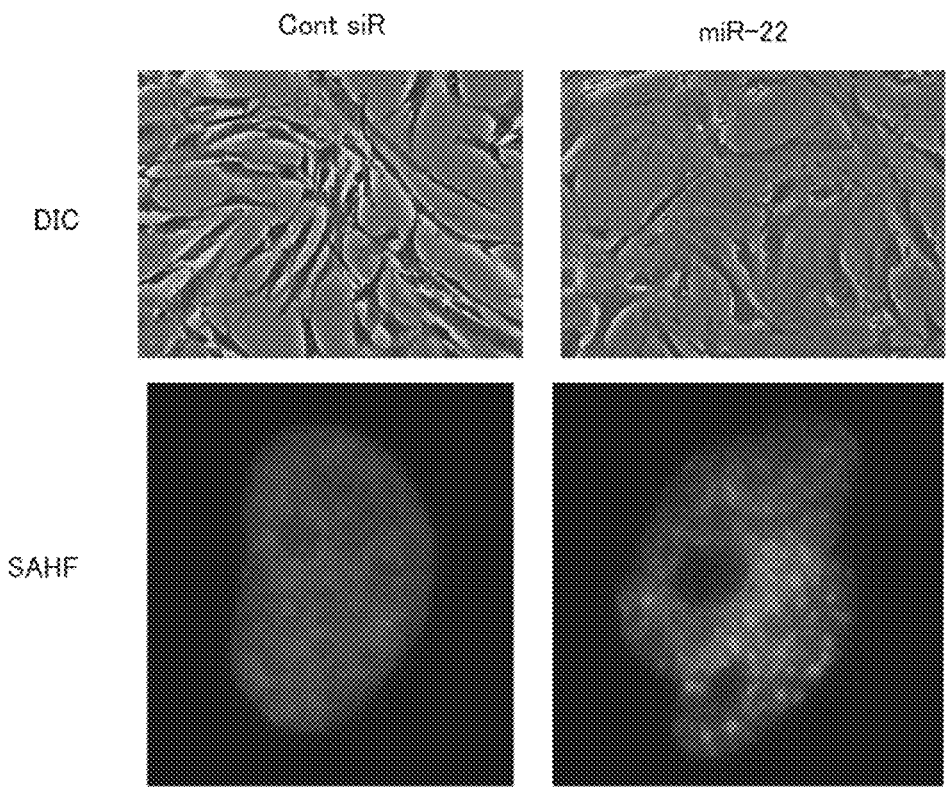
FIG. 4 is a diagram showing images obtained in Example 2 by observation of human fibroblasts into which double-stranded hsa-miR-22 was introduced, which observation was carried out with a fluorescence microscope and a differential interference microscope.

The fixed cells were observed using a differential interference contrast microscope (DIC). Further, the fixed cells were stained with DAPI (4',6-diamidino-2-phenylindole) (0.25 μg/mL) and observed using a fluorescence microscope (Axiovert 200M, Carl Zeiss). FIG. 4 is a diagram showing images obtained in Example 2 by observation of human fibroblasts into which double-stranded hsa-miR-22 was introduced, which observation was carried out with a fluorescence microscope and a differential interference microscope. In FIG. 4, "miR-22" indicates introduction of double-stranded hsa-miR-22 into MRC-5 cells, and "Cont siR" indicates introduction of AllStars Negative Control siRNA (Qiagen) into MRC-5 cells.

As shown in FIG. 4, in the case where double-stranded hsa-miR-22 was introduced into human fibroblasts, the cells showed senescent cell-like largely expanded shapes. Further, formation of SAHF, like those observed in senescent cells, was induced.

Further, the present inventors also investigated whether or not the senescence-associated β-gal activity (hereinafter referred to as the SA-β-gal activity), which is found in senescent cells, is observed in cases where double-stranded hsa-miR-22 was introduced into human fibroblasts (MRC-5 cells).

The experiment was carried out in the same manner as in the above-described detection of SAHF until the step of washing cells twice by addition of PBS. Thereafter, an SA-β-gal staining solution which contains 40 mM citric acid (pH 6.0), 5 mM potassium ferrocyanide, 5 mM potassium ferricyanide, 150 mM NaCl, 2 mM $MgCl_2$ and 0.5 mM/mL 5-bromo-4-chloro-3-indolyl-β-D-galactopyranoside (X-gal) was prepared upon use, and the cells were incubated therein at 37° C. for 48 hours. The stained cells were observed under a conventional microscope, and the number of SA-β-gal-active cells out of 500 cells was counted for evaluation.

Figure 5:
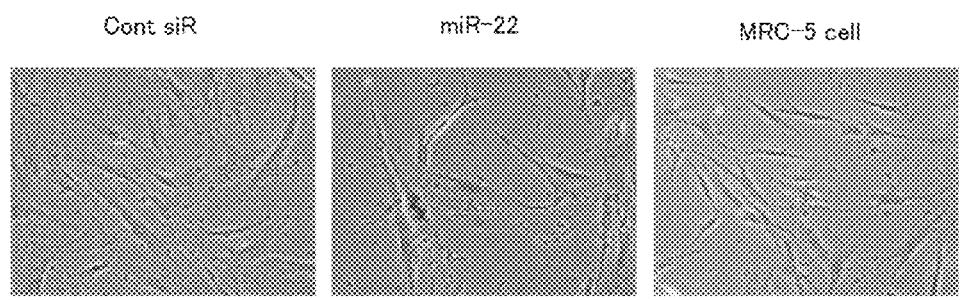
FIG. 5 is a diagram showing images obtained in Example 2 by observation of human fibroblasts into which double-stranded hsa-miR-22 was introduced, which observation was carried out under the microscope after staining the cells for a senescent cell-specific marker SA-β-gal.
Figure 6:
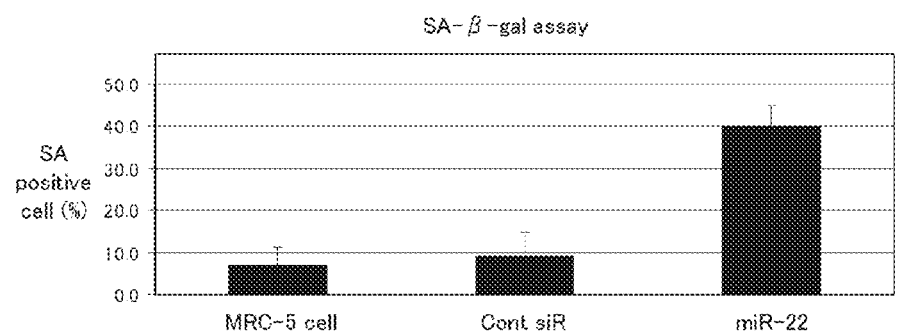
FIG. 6 is a diagram showing data obtained in Example 2 on the ratio of senescent cell-specific-SA-β-gal-active cells in human fibroblasts into which double-stranded hsa-miR-22 was introduced.

FIG. 5 is a diagram showing images obtained in Example 2 by observation of human fibroblasts into which double-stranded hsa-miR-22 was introduced, which observation was carried out under the microscope after staining the cells for a senescent cell-specific marker SA-β-gal. FIG. 6 is a diagram showing data obtained in Example 2 on the ratio of senescent cell-specific-SA-β-gal-active cells in human fibroblasts into which double-stranded hsa-miR-22 was introduced. "MRC-5 cell" shown in FIG. 5 and FIG. 6 indicates the result of observation of cells into which neither double-stranded hsa-miR-22 nor AllStars Negative control siRNA (Qiagen) was introduced. As in FIG. 4, "miR-22" and "Cont siR" indicate the results obtained by introduction of double-stranded hsa-miR-22 or AllStars Negative Control siRNA (Qiagen), respectively, into MRC-5 cells. In FIG. 6, "SA positive cell (%)" represents the ratio (%) of SA-β-gal-active cells. As shown in FIG. 5 and FIG. 6, it was revealed that introduction of double-stranded hsa-miR-22 (miR-22) into human fibroblasts induces the SA-β-gal activity, which is found in senescent cells.

Further, the present inventors studied how the cell growth changes after introduction of double-stranded hsa-miR-22 into human fibroblasts (MRC-5 cells). The experiment was carried out in the same manner as described above until the step of introduction of double-stranded hsa-miR-22. Forty-eight hours after the introduction, $3 \times 10^4$ MRC-5 cells were plated on a 35-mm dish, and cultured for 5 days. In terms of the culture conditions, the medium and conditions were the same as those described in Example 1. During the culture period, cells were collected every 24 hours, and the number of cells was counted. Each experiment was carried out in duplicate. A cell growth curve was prepared based on the result.

Figure 7:
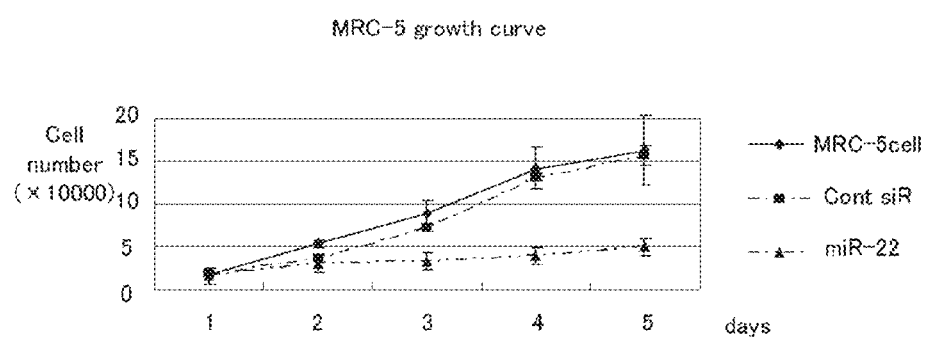
FIG. 7 is a diagram showing data obtained in Example 2 on the cell number of human fibroblasts into which double-stranded hsa-miR-22 was introduced.

FIG. 7 is a diagram showing data obtained in Example 2 on the cell number of human fibroblasts into which double-stranded hsa-miR-22 was introduced. That is, a growth curve of MRC-5 cells (MRC-5 growth curve) is shown. The meanings of "MRC-5 cell", "miR-22" and "Cont siR" in FIG. 7 are the same as in the above-described FIG. 5 and FIG. 6. As shown in FIG. 7, the number of cells (Cell number) into which double-stranded hsa-miR-22 was introduced (miR-22) hardly changed. That is, it was revealed that, by introduction of double-stranded hsa-miR-22 (miR-22), growth of human fibroblasts (MRC-5 cells) is inhibited.

Further, the present inventors investigated the influence of introduction of double-stranded hsa-miR-22 into human fibroblasts (MRC-5 cells) on expression of a cell cycle factor p21, a cyclin-dependent kinase CDK6 (cyclin-dependent kinase 6) and the like.

In the same manner as described above, double-stranded hsa-miR-22 was introduced into human fibroblasts (MRC-5 cells), and the cells after the introduction were recovered by centrifugation and solubilized (50 mM Tris-HCl pH 8.0, 120 mM NaCl, 1% NP40, 100 mM NaF, 0.2 mM $Na_3VO_4$, 1×complete mini (Roche)). Total protein (30 μg) in the solubilized cells was separated by SDS-PAGE (SDS-Poly-Acrylamide Gel Electrophoresis) and transferred onto PVDF (PolyVinylidene DiFluoride) membrane. Before addition of a primary antibody p53 (clone BP53-12, upstate), p21Waf1/cip1 (DCS360, cell signaling) and CDK6 (C-21, santa cruz), the membrane was blocked with PBS-T (0.05% Tween 20) supplemented with 5% skim milk. Binding of the antibody was visualized using an HRP (horseradish peroxidase)-conjugated secondary antibody. Signals were visualized using ECL plus Kit (Amersham) to be detected. As a control for electrophoresis, β-actin was detected using a monoclonal antibody specific to β-actin (clone AC-15, Sigma).

Figure 8:
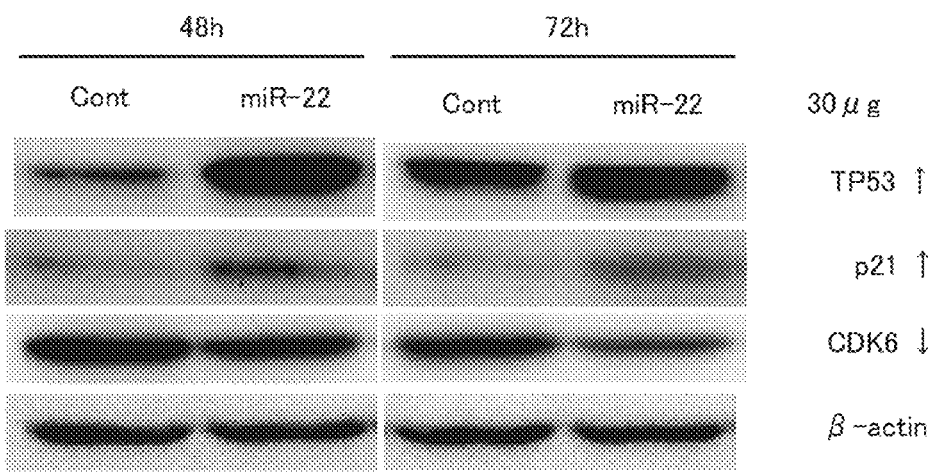
FIG. 8 is a diagram showing images obtained in Example 2 by Western blotting with human fibroblasts into which double-stranded hsa-miR-22 was introduced.

FIG. 8 is a diagram showing images obtained in Example 2 by Western blotting with human fibroblasts into which double-stranded hsa-miR-22 was introduced. In FIG. 8, "Cont" indicates results of electrophoresis of proteins (30 µg) in MRC-5 cells, and "miR-22" indicates results of electrophoresis of proteins (30 µg) in MRC-5 cells into which double-stranded hsa-miR-22 was introduced. As shown in FIG. 8, it was revealed that introduction of double-stranded hsa-miR-22(miR-22) induces expression of the TP53 gene and a cell cycle inhibitor p21, and suppresses expression of a cyclin-dependent kinase CDK6.

From the results of the present Example 2 shown in FIG. 4 to FIG. 8, it was revealed that miR-22 is a miRNA involved in cellular senescence, and that introduction of double-stranded miR-22 into fibroblasts promotes senescence of the cells, causing the cells to have characteristics similar to those of senescent cells, resulting in inhibition of the cell growth (termination of the cell growth).

Example 3

The present Example 3 describes an example in relation to cases where Pre-hsa-miR-22 (see FIG. 1) was introduced into human fibroblasts (MRC-5 cells) by lentivirus infection. The present inventors confirmed whether or not phenomena that specifically accompany cellular senescence (the SA-β-gal activity and inhibition of the cell growth) are observed when Pre-hsa-miR-22, which is a precursor of mature hsa-miR-22, was introduced into human fibroblasts.

First, Lipofectamine LTX Plus reagent (Invitrogen) was used to cotransfect 293T cells with 0.9 µg of Pre-hsa-miR-22 or a lentivirus vector as a control empty vector (these were manufactured by System Biosciences), and 0.9 µg of a packaging plasmid mix (pPACK-H1-GAG, pPACK-H1-Rev and pVSV-G), thereby producing a lentivirus. Forty-eight hours after the transfection, the supernatant obtained by filtration through a 0.45 µm filter was collected, and the collected supernatant was directly used for infection of MRC-5 cells. Although not shown in the figure, transduction and transcription of the vector were confirmed by quantitative real-time PCR and under a fluorescence microscope.

Figure 9:
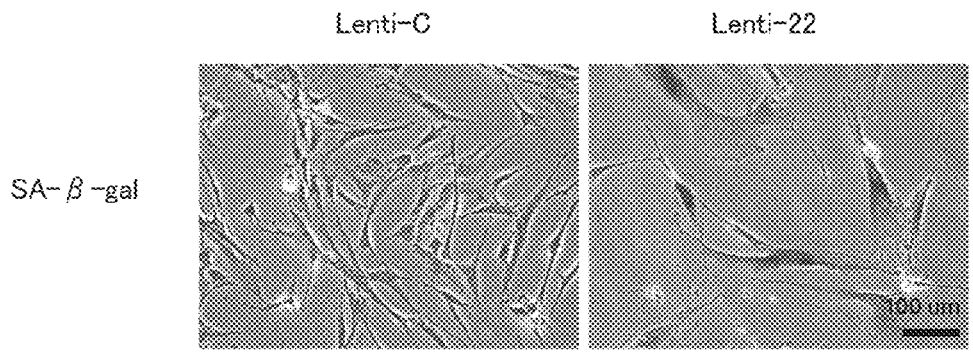
FIG. 9 is a diagram showing images obtained in Example 3 by observation of human fibroblasts into which Pre-hsa-miR-22 was introduced, which observation was carried out under the microscope after staining the cells for a senescent cell-specific marker SA-β-gal.
Figure 10:
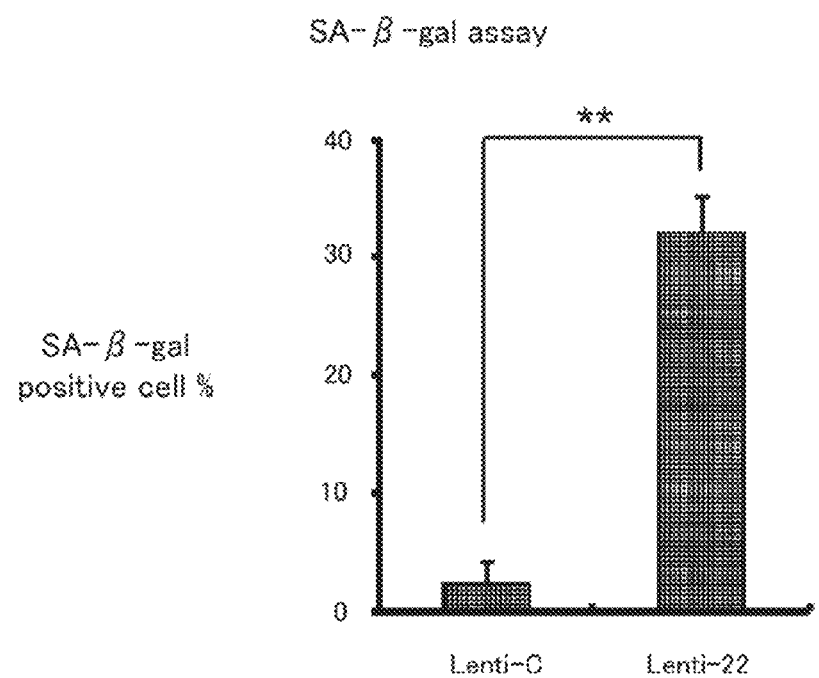
FIG. 10 is a diagram showing data obtained in Example 3 on the ratio of senescent cell-specific-SA-β-gal-active cells in human fibroblasts into which Pre-hsa-miR-22 was introduced.

The staining method for detection of the SA-β-gal activity and the method of counting/evaluation of the active cells were the same as in the above-described case in Example 2 where double-stranded hsa-miR-22 was introduced. FIG. 9 is a diagram showing images obtained in Example 3 by observation of human fibroblasts into which Pre-hsa-miR-22 was introduced, which observation was carried out under the microscope after staining the cells for a senescent cell-specific marker SA-β-gal. FIG. 10 is a diagram showing data obtained in Example 3 on the ratio of senescent cell-specific-SA-β-gal-active cells in human fibroblasts into which Pre-hsa-miR-22 was introduced.

As shown in FIG. 9 and FIG. 10, the MRC-5 cells into which Pre-hsa-miR-22 was introduced by lentivirus infection (Lenti-22) showed a lower ratio of SA-β-gal-active cells than the MRC-cells to which the control empty vector was introduced (Lenti-C).

In a similar manner, using MRC-5 cells into which Pre-hsa-miR-22 was introduced by lentivirus infection, changes in the cell growth were investigated. The method for culturing the cells, the method for preparing a growth curve of the cells, and the like were the same as those described above in Example 2.

Figure 11:
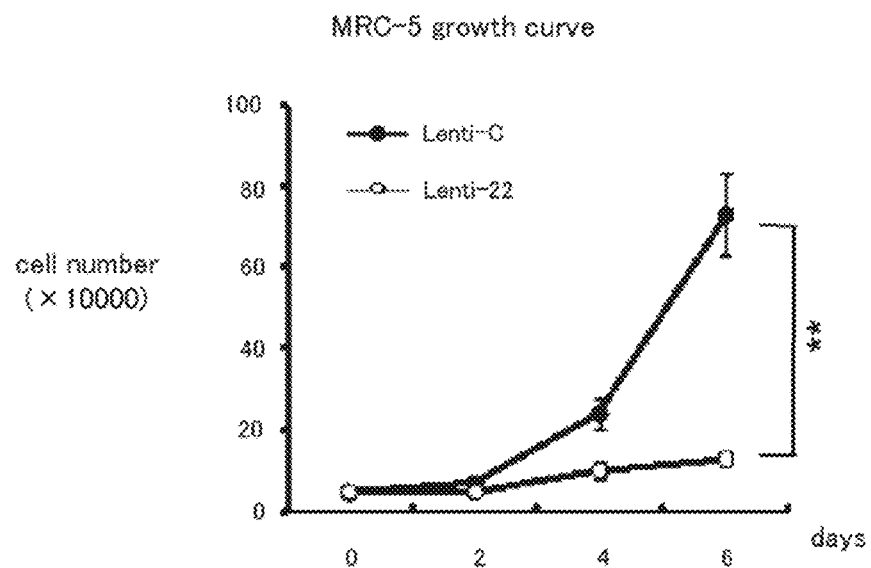
FIG. 11 is a diagram showing data obtained in Example 3 on the cell number of human fibroblasts into which Pre-hsa-miR-22 was introduced.

FIG. 11 is a diagram showing data obtained in Example 3 on the cell number of human fibroblasts into which Pre-hsa-miR-22 was introduced. As shown in FIG. 11, similarly to the case where double-stranded hsa-miR-22 was introduced, the growth the MRC-5 cells into which Pre-hsa-miR-22 was introduced (Lenti-22) was also inhibited relative to the case of the MRC-cells into which the control empty vector was introduced (Lenti-C).

From the results shown in FIG. 9 to FIG. 11, it was revealed that, similarly to cases where double-stranded hsa-miR-22 was introduced into human fibroblasts, introduction of Pre-hsa-miR-22 into human fibroblasts promotes senescence of the cells, causing the cells to have characteristics similar to those of senescent cells, resulting in inhibition of the cell growth (termination of the cell growth).

Example 4

The present Example 4 describes an example in relation to the expression levels of hsa-miR-22* in cancer cells and normal human fibroblasts. The present inventors considered that the characteristics of miR-22 to cause cellular senescence and inhibit the cell growth, which were observed as a result of Example 2 and Example 3, may also have an influence on cancer cells. In view of this, the present inventors investigated the expression levels of hsa-miR-22* in cancer cells and normal human fibroblasts by quantitative real-time RT-PCR, and compared the results. Details of the investigation are described below.

As human cancer cell lines, gastric cancer (squamous epithelium-type adenocarcinoma) cells (MKN-1 cells), gastric cancer cells (MKN-74 cells), gastric cancer cells (TMK-1 cells), uterine cancer cells (MES-SA cells), pharyngeal cancer cells (KB cells), breast cancer cells (MCF-7 cells), cervical cancer cells (HeLa cells), colon cancer cells (RKO cells) and cervical cancer cells (SiHa cells) were investigated. As normal human fibroblasts, TIG-3p42 cells were used.

The culture conditions for each type of cancer cells and TIG-3p42 cells were the same as those for TIG-3 cells and the like described in Example 1. The methods of recovery of RNA from these cells after culturing, and quantitative real-time RT-PCR were also the same as those in Example 1.

Figure 12:
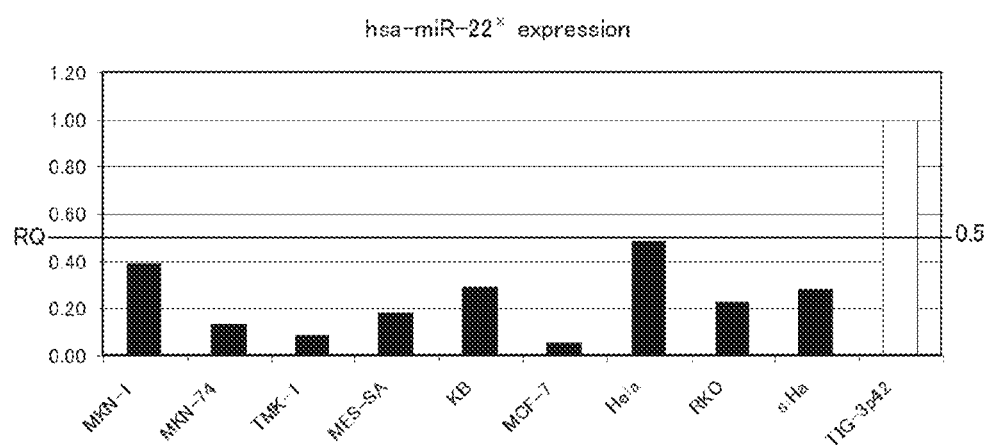
FIG. 12 is a diagram showing data on the expression levels of hsa-miR-22* in cancer cells and human normal fibroblasts measured by qRT-PCR in Example 4.

FIG. 12 is a diagram showing data on the expression levels of hsa-miR-22* in cancer cells and normal human fibroblasts measured by qRT-PCR in Example 4. As shown in FIG. 12, the relative value calculated taking the expression level of hsa-miR-22* in TIG-3p42 cells as 1 (RQ (relative quantitation)) was less than 0.5 in all the types of cancer cells. That is, it was revealed from the present Example 4 that the expression level of miR-22 is low in cancer cells, and miR-22 is hardly functioning in the cells.

Example 5

The present Example 5 describes an example in relation to cases where double-stranded hsa-miR-22 was introduced into cancer cells. From the above-described result of Example 4, the present inventors considered that the phenomenon of growth of cancer cells may be related to low expression of miR-22. In view of this, the present inventors investigated whether or not phenomena found in senescent cells are observed after introduction of double-stranded hsa-miR-22 into cancer cells. Details of the investigation are described below.

Figure 13:
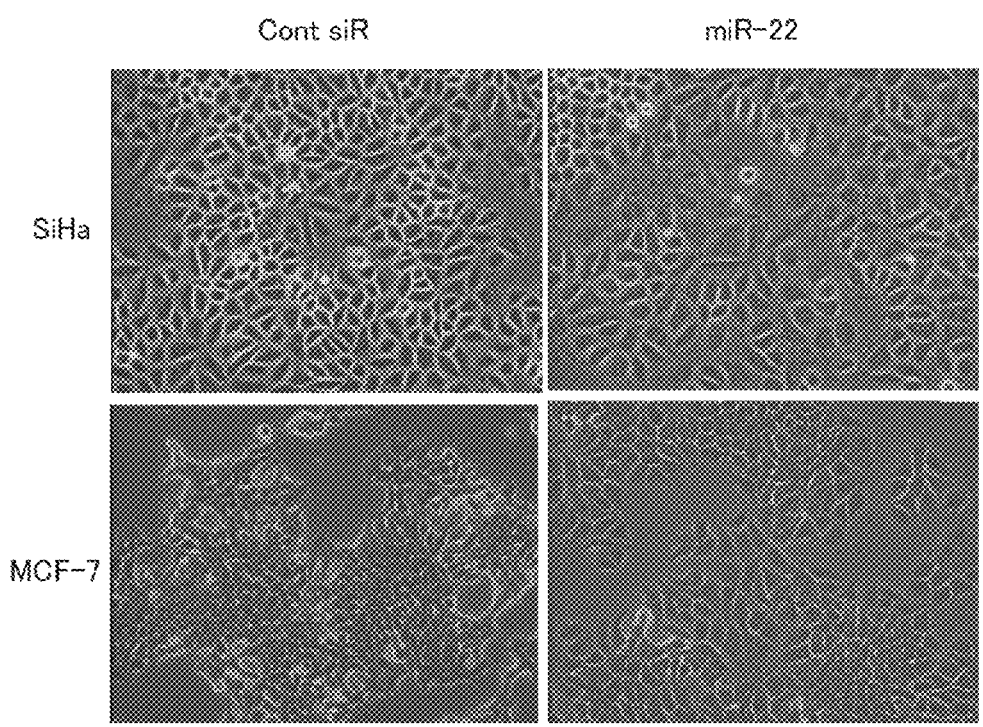
FIG. 13 is a diagram showing images obtained in Example 5 by observation of cancer cells into which double-stranded hsa-miR-22 was introduced, which observation was carried out with a differential interference microscope.

As cancer cells, SiHa cells and MCF-7 cells were used. The culture conditions for these cancer cells were the same as those for TIG-3 cells and the like described in Example 1. The method of introduction of double-stranded hsa-miR-22 into the cancer cells was the same as in the above-described Example 2. FIG. 13 is a diagram showing images obtained in Example 5 by observation of cancer cells into which double-stranded hsa-miR-22 was introduced, which observation was carried out with a differential interference microscope. In FIG. 13, "miR-22" indicates introduction of double-stranded hsa-miR-22 into SiHa cells or MCF-7 cells. "Cont siR" indicates introduction of AllStars Negative Control siRNA (Qiagen) into SiHa cells or MCF-7 cells. As shown in FIG. 13, introduction of double-stranded hsa-miR-22 (miR-22 cells) into the cancer cells (SiHa cells and MCF-7 cells) induced the cells to exhibit largely expanded shapes similar to those of senescent cells.

Further, the present inventors investigated whether or not the SA-β-gal activity, which is found in senescent cells, is observed in cases where double-stranded hsa-miR-22 was introduced into cancer cells (SiHa cells and MCF-7 cells) in the same manner as in the above Example 2. The culture conditions for the cancer cells were the same as those for TIG-3 cells and the like described in Example 1, and the method of measurement of the SA-β-gal activity was the same as in Example 2.

Figure 14:
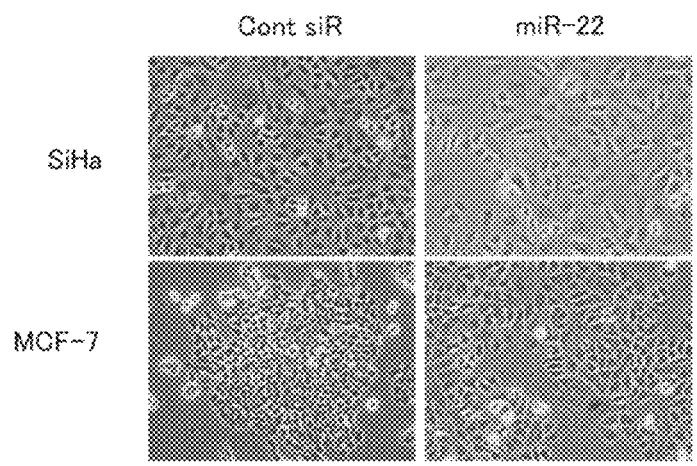
FIG. 14 is a diagram showing images obtained in Example 5 by observation of cancer cells into which double-stranded hsa-miR-22 was introduced, which observation was carried out under the microscope after staining the cells for a senescent cell-specific marker SA-β-gal.
Figure 15:
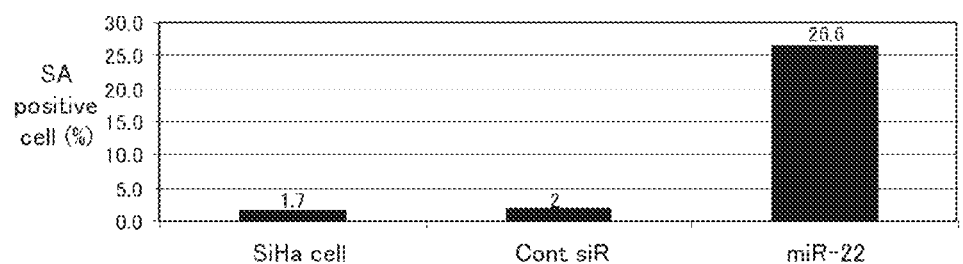
FIG. 15 is a diagram showing data obtained in Example 5 on the ratio of senescent cell-specific-SA-β-gal-active cells in SiHa cells into which double-stranded hsa-miR-22 was introduced.
Figure 16:
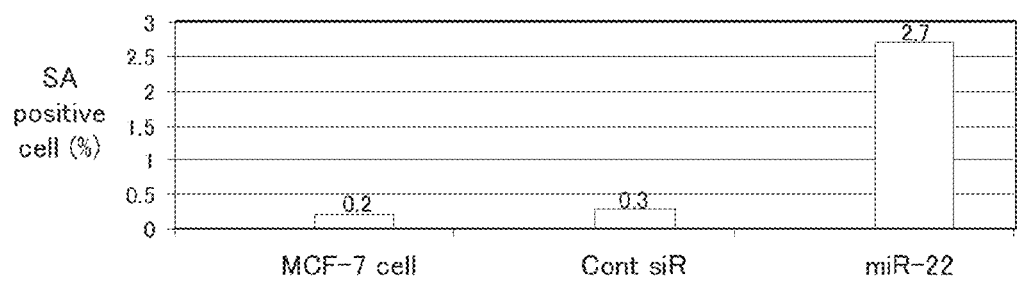
FIG. 16 is a diagram showing data obtained in Example 5 on the ratio of senescent cell-specific-SA-β-gal-active cells in MCF-7 cells into which double-stranded hsa-miR-22 was introduced.

FIG. 14 is a diagram showing images obtained in Example 5 by observation of the cancer cells into which double-stranded hsa-miR-22 was introduced, which observation was carried out under the microscope after staining the cells for a senescent cell-specific marker SA-β-gal. FIG. 15 is a diagram showing data obtained in Example 5 on the ratio of senescent cell-specific-SA-β-gal-active cells in SiHa cells into which double-stranded hsa-miR-22 was introduced. FIG. 16 is a diagram showing data obtained in Example 5 on the ratio of senescent cell-specific-SA-β-gal-active cells in MCF-7 cells into which double-stranded hsa-miR-22 was introduced. In FIG. 14 to FIG. 16, "miR-22" and "Cont siR" have the same meanings as in the above FIG. 13. In FIG. 15 and FIG. 16, both "SiHa cell" and "MCF-7 cell" indicate results of observation by introduction of neither of these.

As shown in FIG. 14 to FIG. 16, it was revealed that introduction of double-stranded hsa-miR-22 (miR-22) into cancer cells (SiHa cells and MCF-7 cells) induces the SA-β-gal activity, which is found in senescent cells.

Further, the present inventors studied how the growth of the cancer cells changes after introduction of double-stranded hsa-miR-22 into the cancer cells (SiHa cells and MCF-7 cells). The experiment was carried out in the same manner as described above until the step of introduction of double-stranded hsa-miR-22, and culture was carried out in the same manner as described in Example 2 for 5 days. Based on the obtained result, a growth curve of the cells was prepared. Further, on Day 7 of the culture after the introduction, appearance of the cancer cells was observed under a differential interference microscope.

Figure 17:
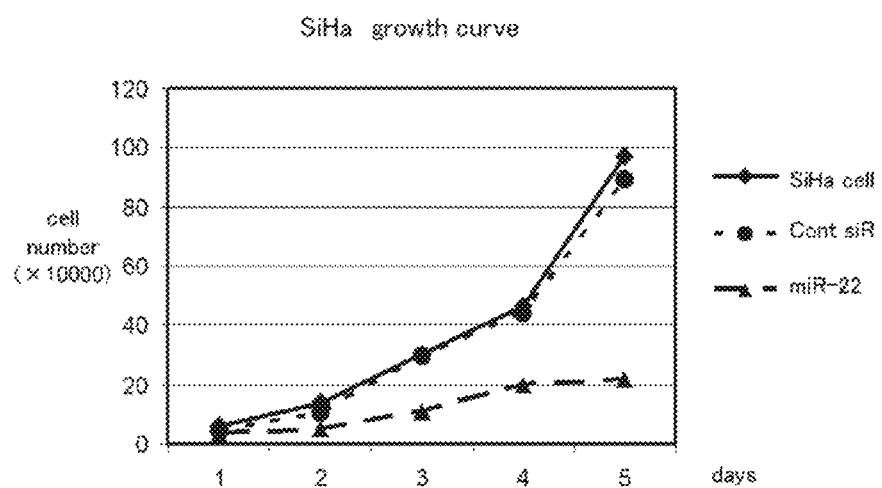
FIG. 17 is a diagram showing data obtained in Example 5 on the cell number of SiHa cells into which double-stranded hsa-miR-22 was introduced.
Figure 18:
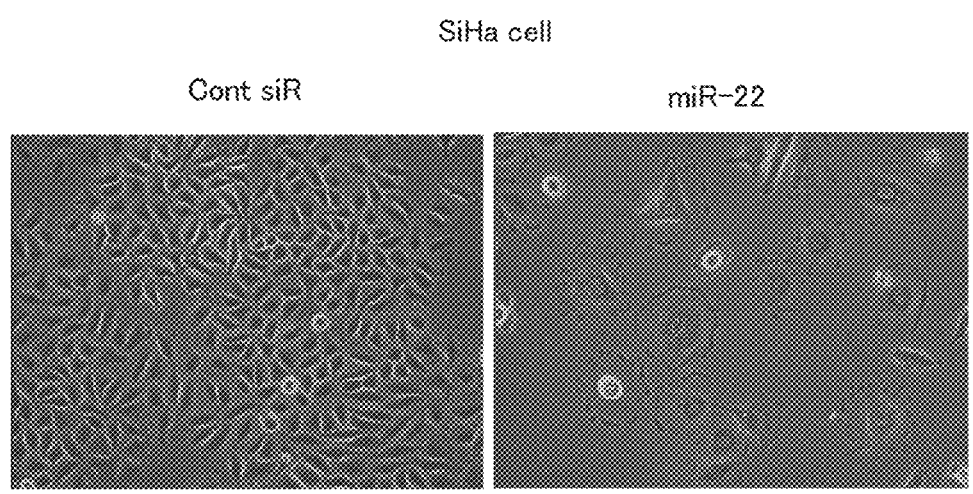
FIG. 18 is a diagram showing images obtained in Example 5 by introducing double-stranded hsa-miR-22 to SiHa cells and culturing the resulting cells for 7 days, followed by observing the cells with a differential interference microscope.
Figure 19:
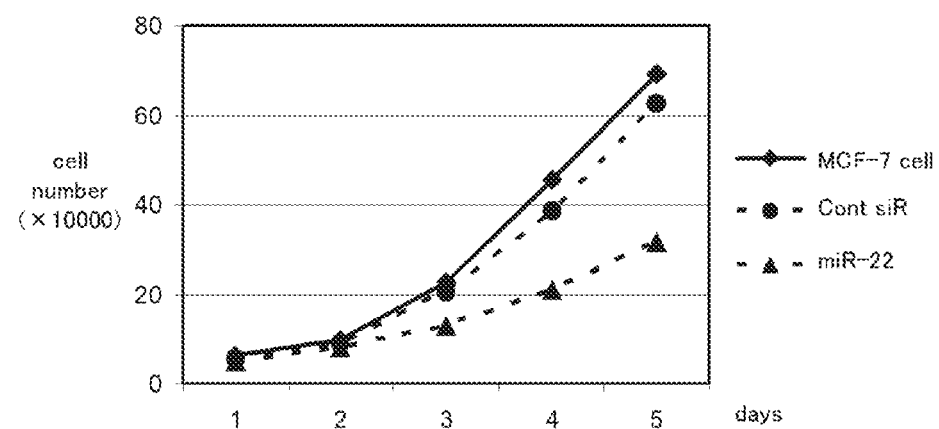
FIG. 19 is a diagram showing data obtained in Example 5 on the cell number of MCF-7 cells into which double-stranded hsa-miR-22 was introduced.
Figure 20:
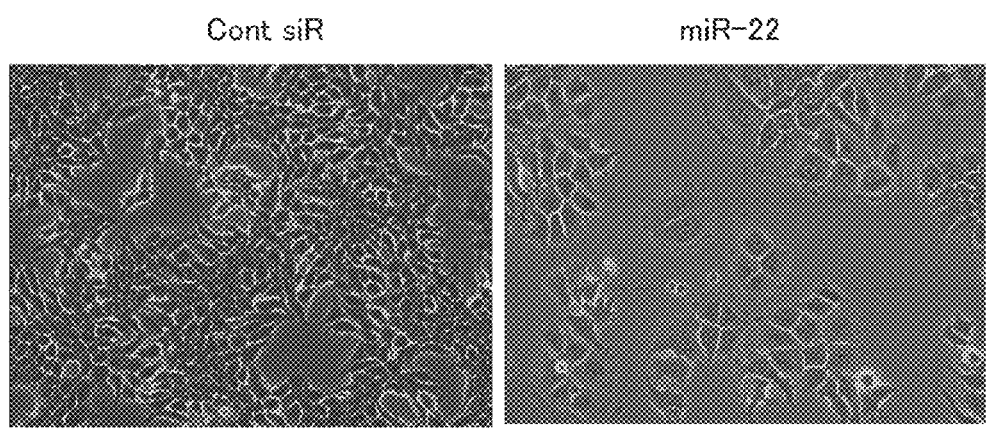
FIG. 20 is a diagram showing images obtained in Example 5 by introducing double-stranded hsa-miR-22 into MCF-7 cells and culturing the resulting cells for 7 days, followed by observing the cells with a differential interference microscope.

FIG. 17 is a diagram showing data obtained in Example 5 on the cell number of SiHa cells into which double-stranded hsa-miR-22 was introduced. That is, a growth curve of the SiHa cells (SiHa growth curve) is shown. FIG. 18 is a diagram showing images obtained in Example 5 by introducing double-stranded hsa-miR-22 to SiHa cells and culturing the resulting cells for 7 days, followed by observing the cells with a differential interference microscope. FIG. 19 is a diagram showing data obtained in Example 5 on the cell number of MCF-7 cells into which double-stranded hsa-miR-22 was introduced. That is, a growth curve of the MCF-7 cells (MCF-7 growth curve) is shown. FIG. 20 is a diagram showing images obtained in Example 5 by introducing double-stranded hsa-miR-22 into MCF-7 cells and culturing the resulting cells for 7 days, followed by observing the cells with a differential interference microscope. The meanings of "miR-22" and "Cont siR" in FIG. 17 to FIG. 20 are the same as in FIG. 13, and the meanings of "SiHa cell" and "MCF-7 cell" are the same as in FIG. 15 or FIG. 16.

As shown in FIG. 17 and FIG. 19, although the SiHa cells and MCF-7 cells (miR-22) into which double-stranded hsa-miR-22 was introduced showed less change in the number of cells (cell number) compared to Cont siR, and SiHa cells or MCF-7 cells, the number of cells was maintained to a certain extent even on Day 5. Further, as shown in FIG. 18 and FIG. 20, the cancer cells (SiHa cells and MCF-7 cells) after introduction of double-stranded hsa-miR-22 showed senescence-associated morphologies on Day 7 of the culture. That is, from the results shown in FIG. 17 to FIG. 20, it was revealed that introduction of double-stranded hsa-miR-22 into cancer cells (SiHa cells or MCF-7 cells) does not promote apoptosis, but promotes cellular senescence, resulting in inhibition of growth of the cancer cells.

From the results of the present Example 5 shown in FIG. 13 to FIG. 20, it was revealed that introduction of double-stranded miR-22 into cancer cells causes the cancer cells to have characteristics similar to those of senescent cells. It was further revealed that introduction of the gene transcript of miR-22 into cancer cells promotes cellular senescence, and, as a result, growth of the cancer cells is inhibited.

Example 6

The present Example 6 describes an example in relation to the invasion capacity of cancer cells into which double-stranded hsa-miR-22 was introduced. From the above-described results of Example 5, the present inventors considered that introduction of double-stranded hsa-miR-22 may not only inhibit growth of cancer cells but also inhibit invasion by cancer cells. In view of this, cellular invasion by cancer cells into which double-stranded hsa-miR-22 was introduced was studied. Details of the study are described below.

As cancer cells, SiHa cells (cervical cancer cells) were used. The culture conditions for the SiHa cells were the same as those for TIG-3 cells and the like described in Example 1. The method of introduction of double-stranded hsa-miR-22 into the cancer cells was the same as that described in Example 2. Forty-eight hours after the introduction, the cultured SiHa cells were plated on a 24-well plate which had been prepared by placing Matrigel in the wells and leaving the plate to stand for 2 hours. The addition of SiHa cells was carried out under serum-free conditions, in an amount of $1.5 \times 10^5$ cells/well. The medium employed contained 10% serum. Subsequently, 48 hours later, the SiHa cells were fixed and cells showing invasion were stained. Thereafter, the number of cells showing invasion was counted.

Figure 21:
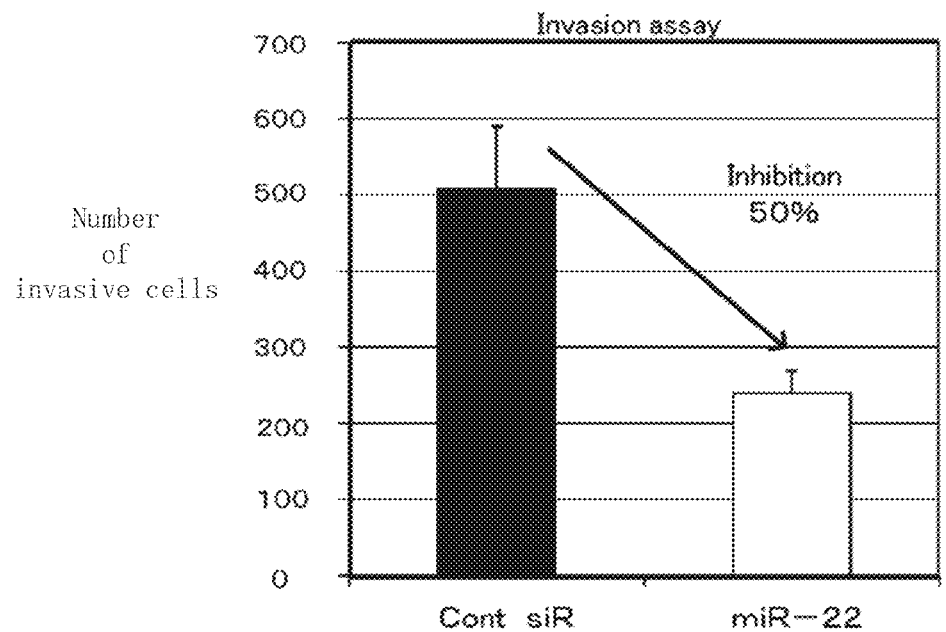
FIG. 21 is a diagram showing data obtained in Example 6 on the number of cells showing invasion among SiHa cells into which double-stranded hsa-miR-22 was introduced.

FIG. 21 is a diagram showing data obtained in Example 6 on the number of cells showing invasion among SiHa cells into which double-stranded hsa-miR-22 was introduced. In FIG. 21, "miR-22" represents SiHa cells into which double-stranded hsa-miR-22 was introduced, and "Cont siR" represents SiHa cells into which AllStars Negative Control siRNA (Qiagen) was introduced. As shown in FIG. 21, in the invasion assay of the SiHa cells of the present Example 6, the number of cells showing invasion decreased in the case of miR-22 by about 50% relative to Cont siR. That is, it was revealed that introduction of double-stranded miR-22 inhibits invasion of cells (cancer cells). Further, it is suggested, based on the result, that introduction of double-stranded miR-22 may inhibit metastasis of cancer cells.

Example 7

The present Example 7 describes an example in relation to the migratory capacity of cancer cells into which double-stranded hsa-miR-22 was introduced (wound-healing assay). In order to further clarify the inhibition of metastasis of cancer cells by introduction of double-stranded hsa-miR-22 suggested by the above-described results of Example 6, the present inventors observed the migratory capacity of cancer cells into which double-stranded hsa-miR-22 was introduced. Details of the observation are described below.

Figure 22:
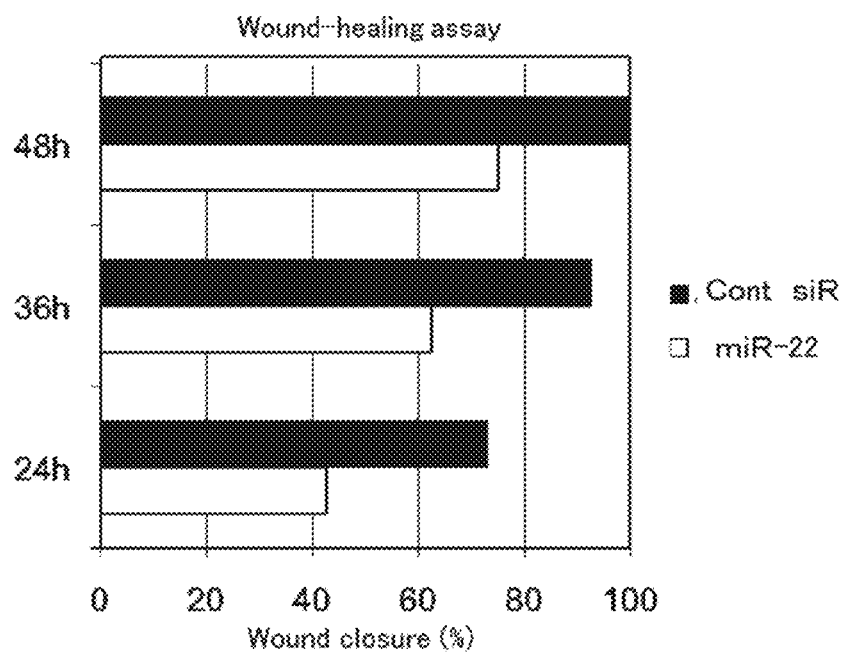
FIG. 22 is a diagram showing data obtained in Example 7 on the ratio of wound closure in a wound healing assay of SiHa cells into which double-stranded hsa-miR-22 was introduced.

As cancer cells, SiHa cells were used. The culture conditions for the SiHa cells were the same as those for TIG-3 cells and the like described in Example 1. The method of introduction of double-stranded hsa-miR-22 into the cancer cells was the same as in the above-described Example 2. Ninety-six hours after the introduction, 100% confluent cells in a 35-mm dish were subjected to treatment by scratching with a sterile 200-μl plastic tip. Thereafter, the ratio of wound closure was monitored from Hour 0 to Hour 48. FIG. 22 is a diagram showing data obtained in Example 7 on the ratio of wound closure in a wound healing assay of SiHa cells into which double-stranded hsa-miR-22 was introduced. In FIG. 22, "miR-22" and "Cont siR" have the same meanings as in the above-described FIG. 21. In FIG. 22, 100(%) corresponds to the state of Cont siR on Hour (h) 48, in which the above-described scratch was completely closed by migration of the cells, although this state is not shown in the figure.

As shown in FIG. 22, based on comparison of the migratory capacity between the SiHa cells of the present Example 7 and Cont siR, it was revealed that SiHa cells to which double-stranded hsa-miR-22 was introduced (miR-22) show inhibition of migration of the cells at any of Hour 24, Hour 36 and Hour 48. Inhibition of the migratory capacity of cells (cancer cells) suggests that the cells (cancer cells) are unlikely to enter into blood vessels (metastasis of cancer is unlikely to occur).

Example 8

In order to more robustly test the effect assumed from the above results in Example 6 and Example 7 by introduction of double-stranded hsa-miR-22 to inhibit growth, invasion and metastasis of cancer, a tumor inhibition test was performed using a subject mouse for breast cancer metastasis. First, in the present Example 8, whether or not phenomena found in senescent cells, and the like are observed as in the above-described Example 5 was confirmed after introduction of double-stranded hsa-miR-22 into MDA-MB-231-luc-D3H2LN breast cancer cells, which were used in the tumor inhibition test and express the firefly luciferase gene. Details of the test are described below.

Figure 23:
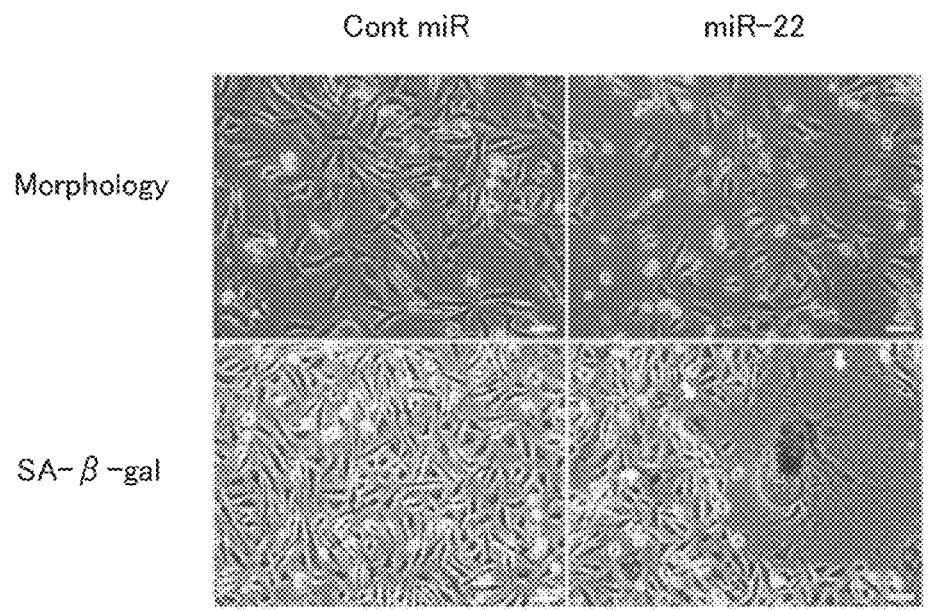
FIG. 23 is a diagram showing images obtained in Example 8 by observation of MDA-MB-231-luc-D3H2LN breast cancer cells into which double-stranded hsa-miR-22 was introduced.

MDA-MB-231-luc-D3H2LN breast cancer cells (provided by Xenogen, USA) were cultured under the conditions of 5% $CO_2$, saturated water vapor and 37° C. in a $CO_2$ incubator. The method of introduction of double-stranded hsa-miR-22 into the cancer cells was the same as in the above-described Example 2. FIG. 23 is a diagram showing images obtained in Example 8 by observation of MDA-MB-231-luc-D3H2LN breast cancer cells into which double-stranded hsa-miR-22 was introduced. In FIG. 23, "Cont siR" means introduction of a negative control miRNA, and "miR-22" means introduction of double-stranded hsa-miR-22. "Morphology" shows images of morphologies of the MDA-MB-231-luc-D3H2LN breast cancer cells into which the negative control miRNA or double-stranded hsa-miR-22 was introduced, which observation was carried out with a differential interference microscope. "SA-β-gal" shows images of these cells stained for SA-β-gal. The method of observation of the SA-β-gal activity was the same as described in Example 2, and the area marked by an arrowhead indicates cells stained for their SA-β-gal activity. In FIG. 23, the white bar shown in the bottom right of each of the four images has an actual length of 20 μm.

As shown in FIG. 23, it was revealed that introduction of double-stranded hsa-miR-22 into MDA-MB-231-luc-D3H2LN breast cancer cells induces the cells to exhibit largely expanded shapes similar to those of senescent cells. Further, it was revealed that the SA-β-gal activity, which is found in senescent cells, is induced. That is, promotion of cellular senescence by introduction of double-stranded hsa-miR-22 could be confirmed also for these breast cancer cells.

Example 9

The present Example 9 describes an example in relation to details of the tumor inhibition test with the model mouse for breast cancer metastasis. For testing the effect of inhibition of growth, invasion and metastasis of cancer by introduction (administration) of double-stranded hsa-miR-22 in vivo, the above-described MDA-MB-231-luc-D3H2LN breast cancer cells that express firefly luciferase were used to perform an expression analysis of the firefly luciferase gene in the model mouse. Details of the analysis are described below.

First, a model mouse for breast cancer metastasis was prepared. As a model mouse, female C.B17/lcr-scid (Scid/scid) mice (5 weeks old, CLEA Inc.) were used. To the adipose tissue of each mouse, the complex of the above MDA-MB-231-luc-D3H2LN breast cancer cells ($2 \times 10^6$ cells/50 μl/site) and ECM gel (cell suspension:ECM gel=1:1) was orthotopically transplanted. The day of transplantation of the cancer cells was regarded as Day 0. Six individual mice were observed for administration of a negative control miRNA and administration of double-stranded hsa-miR-22.

In terms of the administration method, 100 μl (20 μg/site) of the complex of a miRNA selected from a negative control miRNA and double-stranded hsa-miR-22, and jetPEI (in vivo-jetPEI:Polyplus Transfection=1:1) was injected into the tumor. The administration was performed from Day 13 after the transplantation of cancer cells, every other day, that is, 3 times per week, a total of 10 times (Day 13, Day 15, Day 17, Day 19, Day 21, Day 23, Day 25, Day 27, Day 29 and Day 31). Thereafter, on Day 46 after the transplantation of cancer cells, luminescence imaging analysis was carried out in vivo. In the in vivo bioluminescence imaging, D-luciferin (150 mg/kg, Promega, Madison, Wis.) was intraperitoneally administered to each mouse, and, 10 minutes later, the photon value (photon/second, photon quantity) of firefly luciferase was measured using the IVIS imaging system (Xenogen). For data analysis, LivingImage software (version 2.50, Xenogen) was used.

Figure 24:
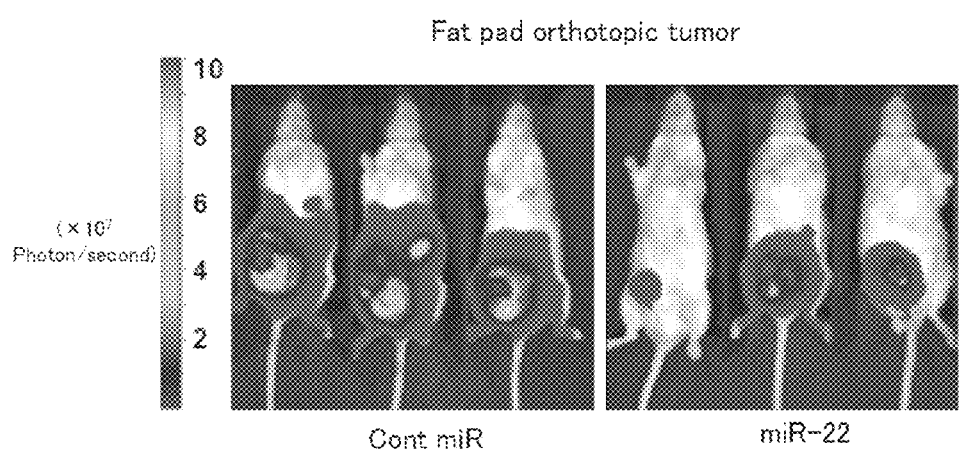
FIG. 24 is a diagram showing images obtained in Example 9 by in vivo luminescence imaging of mice on Day 46 after transplantation of cancer cells.
Figure 25:
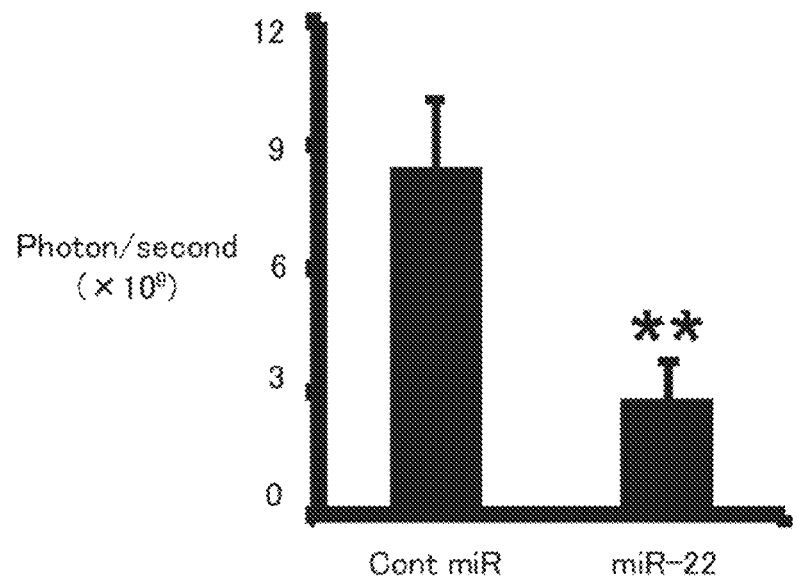
FIG. 25 is a diagram showing data on the photon value measured in Example 9 for mice on Day 46 after transplantation of cancer cells.

FIG. 24 is a diagram showing images obtained in Example 9 by in vivo luminescence imaging of mice on Day 46 after transplantation of cancer cells. Results of the in vivo luminescence imaging for 3 individuals out of the 6 individual mice in each group are shown. FIG. 25 is a diagram showing data on the photon value measured in Example 9 for mice on Day 46 after the transplantation of cancer cells. The data are based on the mean photon value in each individual, which was measured for the 6 individuals in each group.

Figure 26:
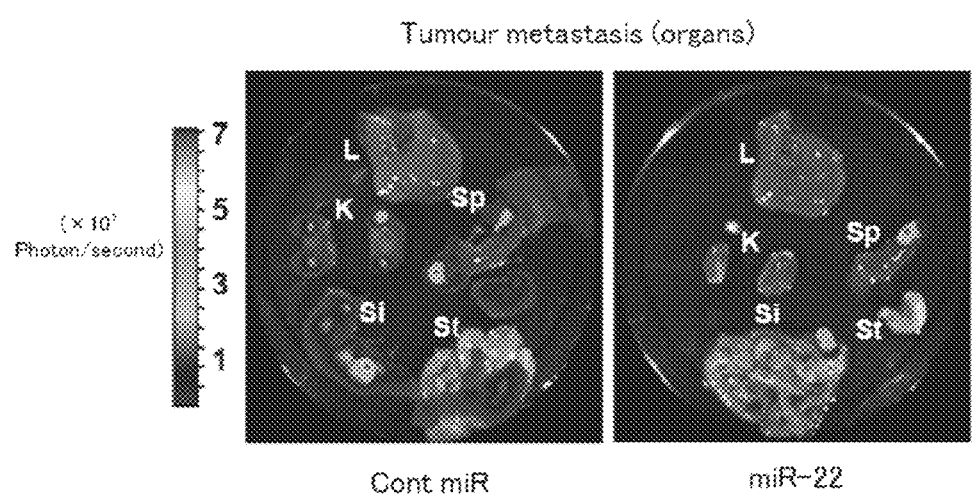
FIG. 26 is a diagram showing images obtained in Example 9 by luminescence imaging of organs of mice on Day 46 after transplantation of cancer cells, which organs were obtained by dissection.
Figure 27:
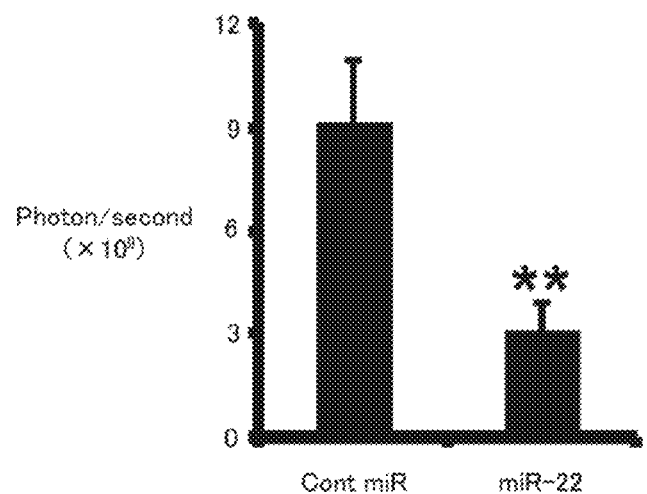
FIG. 27 is a diagram showing data on the photon value measured in Example 9 for organs of mice on Day 46 after transplantation of cancer cells, which organs were obtained by dissection.

FIG. 26 is a diagram showing images obtained in Example 9 by luminescence imaging of mice organs on Day 46 after transplantation of cancer cells, which organs were obtained by dissection. Results of luminescence imaging of tumors in the organs removed from 1 of the 6 mice in each group are shown. Each panel contains images of L (liver), K (kidney), Sp (spleen), St (stomach) and Si (small intestine). FIG. 27 is a diagram showing data on the photon values measured in Example 9 for the organs of mice on Day 46 after the transplantation of cancer cells, which organs were obtained by dissection. The data are based on the mean photon value in each of the 6 individuals in each group, which value was calculated from measurement results for the above-mentioned organs removed by dissection. In FIG. 24 to FIG. 27, "Cont miR" means administration of the complex containing the negative control miRNA, and "miR-22" means administration of the complex containing double-stranded hsa-miR-22.

As shown in FIG. 24 and FIG. 25, when compared to Cont miR, miR-22 exhibited smaller areas of luminescence of firefly luciferase from MDA-MB-231-luc-D3H2LN breast cancer cells, and the total mean photon value in each individual was also small. That is, administration of double-stranded hsa-miR-22 inhibited growth and invasion of the breast cancer cells. Further, as shown in FIG. 26 and FIG. 27, when compared to Cont miR, miR-22 exhibited a smaller number of organs in which luminescence of firefly luciferase could be found among the above-described organs, and the total mean photon value in each dissected individual was also small. That is, administration of double-stranded hsa-miR-22 inhibited growth, invasion and even metastasis of the breast cancer cells.

Example 10

The present Example 10 describes an immunohistochemical example using the above-described model mouse for in vivo breast cancer metastasis in Example 9.

The model mice for breast cancer metastasis prepared in Example 9, that is, Cont miR (prepared by administration of the complex containing a negative control miRNA) and miR-22 (prepared by administration of the complex of double-stranded hsa-miR-22, as a miRNA, and jetPEI) (see FIG. 24 to FIG. 27), were used to perform SA-β-gal staining and HE (Hematoxylin-Eosin) staining of sections of tumor sites in vivo (in vivo-jetPEI:Polyplus Transfection=1:1). The method of the SA-β-gal staining was the same as the above method in Example 2. The HE staining was performed according to a common staining method comprising the steps of staining with hematoxylin and eosin, rinsing with water, dehydration, clearing and mounting, and this was followed by observation of the prepared sections under the microscope.

Figure 28:
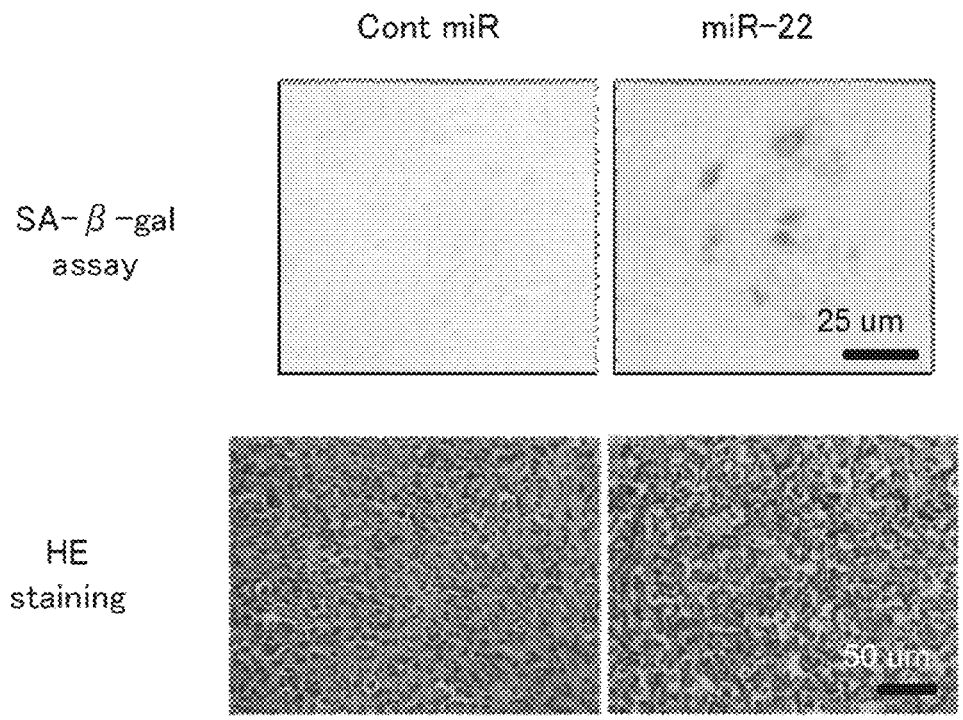
FIG. 28 is a diagram showing images obtained in Example 10 by SA-β-gal staining and HE staining of a tumor site in vivo.

FIG. 28 is a diagram showing images obtained in Example 10 by SA-β-gal staining and HE staining in vivo. As shown in FIG. 28, in the model mouse for the negative control miRNA (Cont miR), induction of senescence was hardly observed by the SA-β-gal assay and HE staining. In contrast, in the mice to which the complex containing double-stranded hsa-miR-22 was administered (miR-22), induction of senescence was observed as shown by the results of the SA-β-gal assay and HE staining. From these results of the in vivo experiment, it was strongly suggested that the above-described inhibition of growth, invasion and metastasis of the breast cancer cells in Example 9 was achieved by induction of cellular senescence.

Example 11

In the present Example 11, MultiTox assay was performed in order to confirm the result in Example 10, which suggested that apoptosis did not occur in the SiHa cells into which double-stranded hsa-miR-22 was introduced.

MultiTox assay (cell cytotoxicity assay, Promega) was performed by a method common to those skilled in the art, to measure the fluorescence intensity and luminescence intensity in the same wells. As controls, miR-34a, which is a miRNA known to induce apoptosis, and a negative control miRNA were used.

Figure 29:
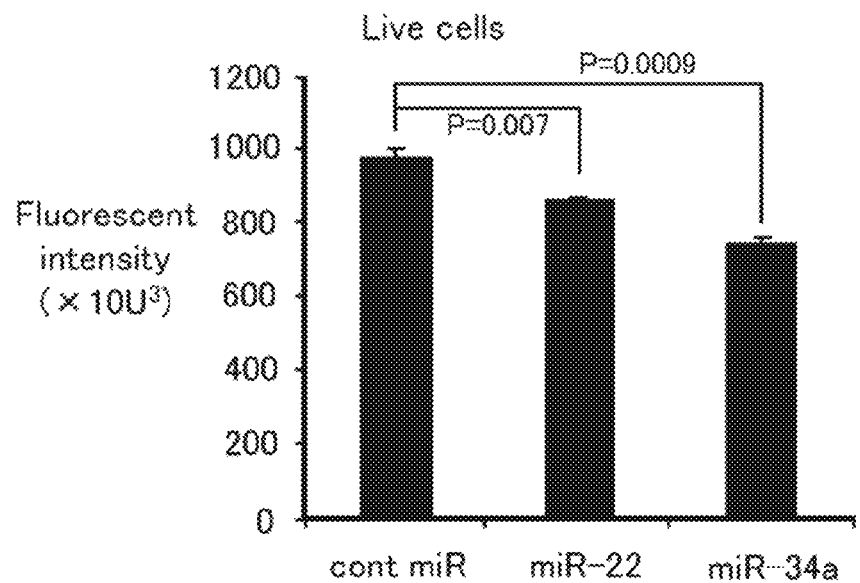
FIG. 29 is a diagram showing data obtained in Example 11 as a result of MultiTox assay of SiHa cells into which double-stranded hsa-miR-22 was introduced, which data were obtained for living cells.
Figure 30:
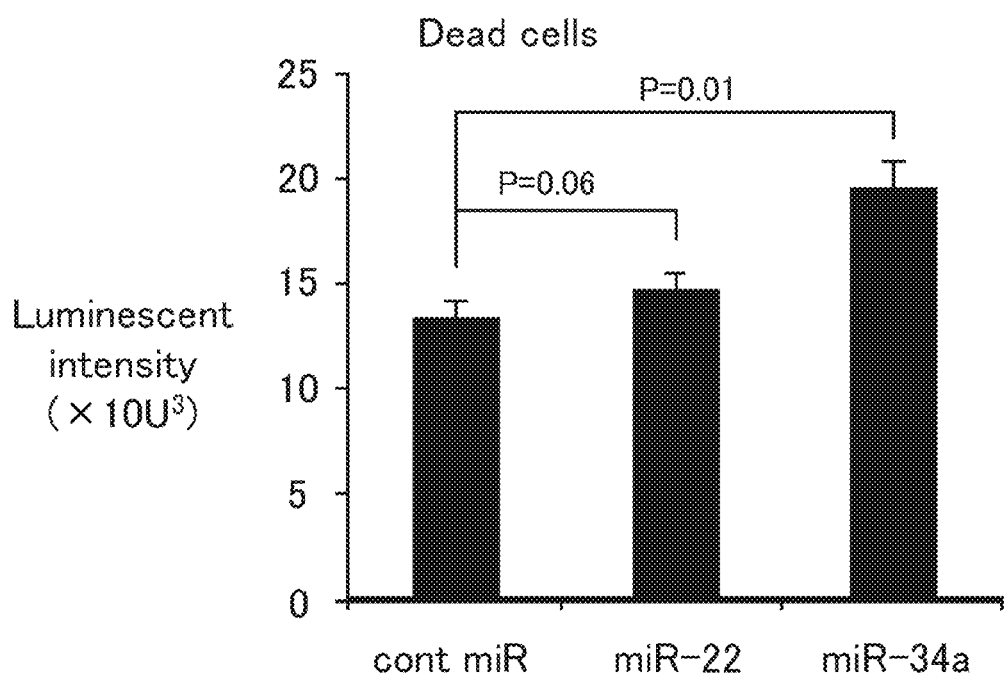
FIG. 30 is a diagram showing data obtained in Example 11 as a result of MultiTox assay of SiHa cells into which double-stranded hsa-miR-22 was introduced, which data were obtained for dead cells.

FIG. 29 is a diagram showing data obtained in Example 11 as a result of MultiTox assay of SiHa cells into which double-stranded hsa-miR-22 was introduced, which data were obtained for living cells. On the other hand, FIG. 30 is a diagram showing data obtained in Example 11 as a result of MultiTox assay of SiHa cells into which double-stranded hsa-miR-22 was introduced, which data were obtained for dead cells. As shown in FIG. 29, based on the result of measurement of the fluorescent intensity ($\times 10^3$ U) reflecting the number of living cells, it could be confirmed that the number of living cells of SiHa cells into which double-stranded hsa-miR-22(miR-22) was introduced was larger than living cells of SiHa cells into which miR-34a, which induces apoptosis, was introduced, and that the difference in the number of living cells of SiHa cells is small between the former cells and SiHa cells into which the negative control miRNA (Cont miR) was introduced. On the other hand, as shown in FIG. 30, based on the result of measurement of the luminescent intensity ($\times 10^3$ U) reflecting the number of dead cells, it could be confirmed that the number of dead cells of SiHa cells into which miR-22 was introduced was smaller than the number of dead cells of SiHa cells into which miR-34a, which induces apoptosis, was introduced, and that the difference in the number of dead cells of SiHa cells is small between the former cells and SiHa cells into which Cont miR was introduced.

Example 12

In order to test, also in the present Example 12, whether apoptosis did not occur in the SiHa cells into which double-stranded hsa-miR-22 was introduced, an example by TUNEL staining was performed.

The cells were stained with DAPI and FITC (fluorescein isothiocyanate), and observed with a fluorescence microscope. The method of fixation of SiHa cells, the method of staining with these dyes, the method of labeling, and the like were the same as those described in Example 2 for human fibroblasts. As controls, miR-34a and a negative control miRNA, which were also used in Example 11, and a positive control were used for comparison.

Figure 31:
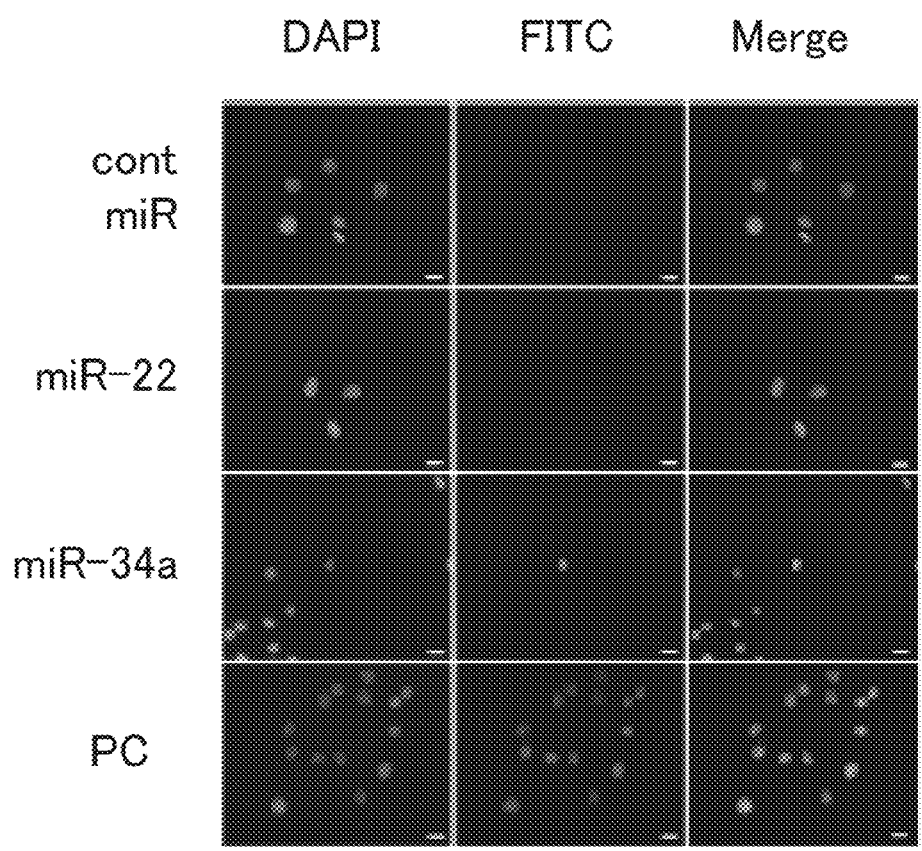
FIG. 31 is a diagram showing images obtained in Example 12 by TUNEL staining of SiHa cells into which double-stranded hsa-miR-22 was introduced.

FIG. 31 is a diagram showing images obtained in Example 12 by TUNEL staining of SiHa cells into which double-stranded hsa-miR-22 was introduced. As shown in FIG. 31, miR-22 showed a smaller number of apoptotic cells detected by staining using DAPI and FITC, relative to SiHa cells into which miR-34 was introduced and SiHa cells into which PC (positive control) was introduced. "Merge" shows a superimposed image of DAPI and FITC for the respective types of cells.

From the results of the above Examples, it could be confirmed that inhibition of growth, invasion and metastasis of cancer by a cancer inhibitor containing double-stranded hsa-miR-22 can be achieved not as a result of induction of apoptosis but as a result of promotion of senescence of (cancer) cells. Further, from these results, it is suggested that a cancer inhibitor containing as an effective component Pre-hsa-miR-22 or a gene transcript of miR-22 from a non-human organism may also produce a similar effect.

The present invention is not limited by descriptions in the embodiments of the present invention and the Examples. Various modified modes are also included in the present invention as long as these modes do not depart from descriptions in claims and are within the scope where the modes can be easily inferred by those skilled in the art.

The contents of the papers, laid-open patent applications and patent publications explicitly mentioned in the present description are herein incorporated by reference in their entirety.

The present application is based on Japanese patent application No. 2009-288707, filed on Dec. 21, 2009, and Japanese patent application No. 2010-049928, filed on Mar. 5, 2010. The descriptions, claims and figures in Japanese patent application No. 2009-288707 and Japanese patent application No. 2010-049928 are herein incorporated by reference in their entirety.

INDUSTRIAL APPLICABILITY

By the present invention, a senescence marker with which the degree of senescence (cellular senescence or the like) of a sample can be judged is provided. Further, a method for evaluation and screening of a senescence inhibitor, which method allows evaluation of a substance that can inhibit senescence (cellular senescence or the like), is provided. Further, a cancer inhibitor using the senescence marker, which cancer inhibitor can promote cellular senescence and thereby inhibit growth, invasion and/or metastasis of cancer, is provided.

The invention claimed is:

1. A method for treating gastric cancer or pharyngeal cancer, comprising the steps of:
   administering to a patient in need thereof a gene transcript of miR-22, and
   promoting cellular senescence and inhibiting invasion and/or metastasis of cancer.

2. The method according to claim 1, wherein said gene transcript of miR-22 comprises RNA having the sequence of SEQ ID NO:1, RNA having the sequence of SEQ ID NO:2, and/or RNA having the sequence of SEQ ID NO:3.

3. The method according to claim 1, wherein said gene transcript of miR-22 comprises Pre-hsa-miR-22 and/or double-stranded hsa-miR-22.

4. The method according to claim 1, wherein the cancer is gastric cancer.

5. The method according to claim 1, wherein the cancer is pharyngeal cancer.

* * * * *

SEQUENCE LISTING

```
<160> NUMBER OF SEQ ID NOS: 3

<210> SEQ ID NO 1
<211> LENGTH: 85
<212> TYPE: RNA
<213> ORGANISM: Homo sapiens

<400> SEQUENCE: 1
ggcugagccg caguaguucu ucaguggcaa gcuuuauguc cugacccagc uaaagcugcc    60
aguugaagaa cuguugcccu cugcc                                         85

<210> SEQ ID NO 2
<211> LENGTH: 22
<212> TYPE: RNA
<213> ORGANISM: Homo sapiens

<400> SEQUENCE: 2
aagcugccag uugaagaacu gu                                            22

<210> SEQ ID NO 3
<211> LENGTH: 22
<212> TYPE: RNA
<213> ORGANISM: Homo sapiens

<400> SEQUENCE: 3
aguucuucag uggcaagcuu ua                                            22
```